(12) United States Patent
Rosenberg et al.

(10) Patent No.: US 8,380,308 B2
(45) Date of Patent: Feb. 19, 2013

(54) SYSTEMS AND METHODS FOR OPTIMIZING VENTRICULAR PACING BASED ON LEFT ATRIAL ELECTROMECHANICAL ACTIVATION DETECTED BY AN AV GROOVE ELECTRODE

(75) Inventors: Stuart Rosenberg, Castaic, CA (US); Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 99 days.

(21) Appl. No.: 13/074,968

(22) Filed: Mar. 29, 2011

(65) Prior Publication Data

US 2012/0253419 A1    Oct. 4, 2012

(51) Int. Cl.
*A61N 1/00*    (2006.01)
*A61B 5/04*    (2006.01)

(52) U.S. Cl. ............................ 607/9; 600/513
(58) Field of Classification Search .......... 600/508–509; 607/9, 17–18, 22–25
See application file for complete search history.

(56) References Cited

U.S. PATENT DOCUMENTS

| | | | | |
|---|---|---|---|---|
| 6,477,406 B1 | 11/2002 | Turcott | | 600/518 |
| 6,512,952 B2 | 1/2003 | Stahmann et al. | | 607/9 |
| 6,628,988 B2 | 9/2003 | Kramer et al. | | 607/9 |
| 6,643,546 B2 | 11/2003 | Mathis et al. | | 607/9 |
| 7,054,687 B1 | 5/2006 | Andersen et al. | | 607/19 |
| 7,149,579 B1 | 12/2006 | Koh | | 607/19 |
| 7,248,925 B2 | 7/2007 | Bruhns et al. | | 607/25 |
| 7,590,446 B1 | 9/2009 | Min et al. | | 607/9 |
| 2005/0125041 A1 | 6/2005 | Min et al. | | 607/9 |
| 2007/0093872 A1 | 4/2007 | Chirife et al. | | 607/9 |
| 2007/0179390 A1 | 8/2007 | Schecter | | 600/508 |
| 2007/0179541 A1 * | 8/2007 | Prakash et al. | | 607/9 |
| 2008/0306567 A1 | 12/2008 | Park et al. | | 607/27 |
| 2009/0299423 A1 | 12/2009 | Min | | 607/9 |
| 2010/0145405 A1 | 6/2010 | Min et al. | | 607/25 |
| 2011/0022106 A1 | 1/2011 | Min | | 607/14 |
| 2011/0022110 A1 | 1/2011 | Min | | 607/25 |
| 2011/0022112 A1 | 1/2011 | Min | | 607/25 |

* cited by examiner

Primary Examiner — Rex R Holmes

(57) ABSTRACT

Techniques are provided for use with an implantable cardiac stimulation device equipped with a multi-pole left ventricular (LV) lead having a proximal electrode implanted near an atrioventricular (AV) groove of the heart of the patient. A left atrial (LA) cardioelectrical event is sensed using the proximal electrode of the LV lead and a corresponding LA cardiomechanical event is also detected, either using an implantable sensor or an external detection system. The electromechanical activation delay between the LA cardioelectrical event and the corresponding LA cardiomechanical event is determined and then pacing delays are set based on the electromechanical activation delay for use in controlling pacing. The pacing delays can include, e.g., AV delays for use with biventricular cardiac resynchronization therapy (CRT) pacing. Other techniques described herein are directed to exploiting right atrial (RA) cardioelectrical events detected via an RA lead for the purposes of setting pacing delays.

29 Claims, 17 Drawing Sheets

SYSTEMS AND METHODS FOR OPTIMIZING VENTRICULAR PACING BASED ON LEFT ATRIAL ELECTROMECHANICAL ACTIVATION DETECTED BY AN AV GROOVE ELECTRODE

FIELD OF THE INVENTION

The invention generally relates to implantable cardiac stimulation devices such as pacemakers, implantable cardioverter-defibrillators (ICDs) and cardiac resynchronization therapy (CRT) devices and, in particular, to techniques for optimizing and controlling biventricular pacing for use with devices equipped with multi-pole left ventricular (LV) leads.

BACKGROUND OF THE INVENTION

State-of-the-art implantable cardiac stimulation devices are equipped with multi-pole LV leads. Examples include quad-pole LV leads having four electrodes arranged from the distal LV apex to the proximal AV groove. When employed to deliver biventricular pacing in conjunction with an RV lead, it is desirable to determine optimal AV/VV pacing delays. For example, AV/VV pacing delays may be optimized for use with CRT, which seeks to normalize asynchronous cardiac electrical activation and resultant asynchronous contractions associated with congestive heart failure (CHF) by delivering synchronized pacing stimulus to both ventricles. That is, the AV/VV delays are set so as to deliver RV and LV stimulation pulses at optimal times to improve the overall cardiac function within the patient. CRT may have the additional beneficial effect of reducing the susceptibility to life-threatening tachyarrhythmias.

Optimization of AV/VV pacing intervals for use with CRT may also help to increase the number of responders to CRT as well as the quality and degree of response among CRT patients. Present methods of CRT optimization include: echocardiographic assessment of transmitral flow (i.e., the Ritter method); maximization of an echo-based aortic Velocity Time Integral; minimization of echo-assessed LV dyssynchrony; and electrical optimization based on surface electrocardiograms (ECGs/EKGs) or intracardiac electrograms (IEGMs.) Optimization techniques based on IEGMs include various QuickOpt™ techniques developed by the assignee of rights to the present invention, such as those described in U.S. Pat. No. 7,248,925.

Echocardiographic methods directly assess LV function but can be time consuming, operator dependent, and can lead to inconclusive timing recommendations. Electrical-based optimization methods such as QuickOpt™ are generally more convenient to implement, operator independent, and can be automated, but typically do not take into account the resultant LV function or any underlying electromechanical abnormalities and can be intrinsically reliant on the right atrial (RA) activation for timing cycle definition.

Accordingly, it would be desirable to provide AV/VV optimization techniques that have the efficiency and convenience of electrical-based techniques such as QuickOpt™ but also account for electromechanical properties of the heart of the patient. It is to this end that the present invention is generally directed.

SUMMARY OF THE INVENTION

In an exemplary embodiment, a method is provided for use with an implantable cardiac stimulation device equipped with an LV lead having a proximal electrode implanted in or near an atrioventricular (AV) groove of the heart of the patient. Separate RV and RA leads may be provided as well. Briefly, left atrial (LA) cardioelectrical events are sensed using the proximal electrode and corresponding LA cardiomechanical events are also detected, either using an implantable detector or an external detection system. LA electromechanical delays are determined between the LA cardioelectrical events and the LA cardiomechanical events and then pacing delays are set based on the LA electromechanical delays for use in delivering pacing. The pacing delays can include, e.g., AV pacing delays for use with biventricular CRT pacing. The device then delivers and/or controls pacing using the AV pacing delays, alone or in combination with VV pacing delays set using QuickOpt™ or other suitable VV optimization techniques. (Herein, "AV delays" are deemed to include both AV and PV delays, where AV delays follow paced atrial events and PV delays follow sensed atrial events.) Other aspects of the invention are directed to exploiting RA cardioelectrical events detected via the RA lead for the purposes of setting pacing delays.

In an illustrative implementation, the implantable device is a pacemaker, ICD or CRT device equipped with a bipolar RV lead, a bipolar RA lead and a quad-pole LV lead implanted via the coronary sinus (CS.) The quad-pole LV lead includes a proximal (P4) electrode implanted in or near the AV groove. The electrode might alternatively be referred to as an LA ring electrode, if similarly positioned. The various leads preferably include coil electrodes as well. The device housing, case or "can" is also preferably equipped to function as an electrode. The LA cardiomechanical event that is detected represents completion of an atrial kick or closure of the mitral valve. The pacing delays to be set based on the LA electromechanical delay are preferably determined so as to provide for delivery of an LV pacing pulse at a time of optimal left heart filling, as set using various timing values summarized below. By timing the delivery of the LV pacing pulse during optimal left heart filling, it is believed that improved cardiac output can be achieved since the LV is thereby caused to contract when substantially full, hence improving stroke volume. In addition, by timing the LV pacing to optimal LV filling, the contractility, i.e. active force generated during contraction, is enhanced by the Frank-Starling mechanism.

In a first set of exemplary embodiments, an initial calibration procedure is performed following device implant wherein an external "reference" system is used to detect the LA cardiomechanical contraction for use in determining the LA electromechanical delay. The reference system, for example, can employ echocardiography to detect: the onset or completion of the A-wave of transmitral flow measured by using a Pulsed Wave Doppler technique, the mitral valve closure time, or the onset, peak, or completion of the A'-wave of the mitral valve annulus via Tissue Doppler. In other examples, sonocardiography is employ to detect: the first onset time of the S1 heart sound and/or a corresponding mitral valve closure time. In still other examples, the reference system exploits impedance cardiography to detect: the time of maximum cardiogenic impedance or a time of maximum time derivative of cardiogenic impedance between RA and P4 electrodes, indicating completion or onset, respectively, of atrial kick into the ventricles.

During calibration, the implanted device detects LA pace and sense events using a P4 sensing vector such as: the P4-case vector, the P4-RVcoil vector, the P4-RAring vector, vectors between the P4 electrode of the LV lead and any of the other electrodes of the LV lead, such as its tip electrode (D1) or either of its intermediate electrodes (M2, M3), and vectors between the P4 electrode of the LV lead and any of the other electrodes in the heart. Based on the timing of the LA pace and sense events detected via the P4 electrode and the corresponding LA cardiomechanical activation detected using the external detection system, the calibration system determines a set of LA electromechanical delay values referred to herein as Electro-Mechanical Offset Time Estimate (EMOTE) values, which are then used to set AV delays to optimal values. QuickOpt™ or other suitable optimization techniques are used to set the VV delays (VVD) to optimal values and to determine whether the RV or LV should be paced first (i.e. LV pre-excitation vs. RV pre-excitation.) These parameters are then programmed into the device for use in controlling subsequent biventricular CRT pacing.

In one particular EMOTE example, the set of values that are determined include: an EMOTE-1i value representing a time delay from an intrinsic LA depolarization as sensed at P4 to the LA cardiomechanical activation as detected using the reference technique; an EMOTE-2i value representing a time delay from an intrinsic RA depolarization as sensed at P4 to the LA cardiomechanical activation as detected using the reference technique; an EMOTE-1r value representing a time delay from an RA-paced LA depolarization to the LA cardiomechanical activation as detected using the reference technique; and an EMOTE-2r value representing a time delay from an RA pace to the LA cardiomechanical activation as detected using the reference technique.

If the implanted device is equipped to use the RA electrode to detect atrial events via an RA sensing channel during biventricular pacing, the device is programmed to use the aforementioned EMOTE-2 values for setting the AVD because the EMOTE-2 values are more appropriate for use with RA channel sensing. In one particular example, AVD is set equal to EMOTE-2+, where EMOTE-2+ is derived from the aforementioned EMOTE-2 values based on whether the atrial event is paced or sensed. More specifically, EMOTE-2+ is set equal to EMOTE2i plus a programmable offset for use with intrinsic atrial events sensed in the RA. EMOTE-2+ is instead set equal to EMOTE2r plus the offset for use with paced atrial events. That is, EMOTE-2+ can have different values depending on whether the atrial event is paced or sensed. In one specific example, the offset is programmed to 20 milliseconds (ms). This value can be adjusted based on instantaneous heart rate, current patient posture and/or current patient activity level. Having set the value for AVD to EMOTE-2+ for use with RA sensing, the device then controls biventricular CRT pacing based on atrial events sensed using the RA lead by applying the AVD and VVD values to the time of the atrial pace/sense as follows:

For LV first pacing (i.e. LV pre-excitation) based on atrial events sensed via the RA lead where AVD=EMOTE-2+:
pace the LV using AVD (e.g. add AVD to the time of RA depolarization as sensed or paced using the RA lead)
pace RV using AVD+VVD
For RV first pacing (i.e. RV pre-excitation) based on atrial events sensed via the RA lead where AVD=EMOTE-2+:
pace RV using AVD−VVD
pace LV using AVD If the implanted device is additionally or alternatively equipped to use the P4 electrode to detect atrial events via a separate P4 sensing channel during biventricular pacing, the device is instead programmed to use the EMOTE-1 values for setting the AVD because the EMOTE-1 values are more appropriate for use with P4 channel sensing. In one particular example, AVD is set equal to EMOTE-1+, where EMOTE-1+ is derived from the EMOTE-1 values. More specifically, EMOTE-1+ is set equal to EMOTE1i plus a programmable offset for use with intrinsic atrial events sensed in the LA via P4. EMOTE-1+ is instead set equal to EMOTE1r plus the offset for use with paced atrial events. That is, EMOTE-1+ can have different values depending on whether the atrial event is paced or sensed. The offset can again be programmed to 20 ms (adjustable based on heart rate, patient posture and/or activity) for sensed events and 30 ms for paced events. Having set the AVD to EMOTE-1+ for use with P4 sensing, the device then controls biventricular pacing based on atrial events sensed using P4 by applying the AVD and VVD values as follows:

For LV first pacing (i.e. LV pre-excitation) based on atrial events sensed via the P4 electrode where AVD=EMOTE-1+:
pace the LV using AVD (e.g. add AVD to the time of LA depolarization as sensed using the P4 lead while accounting for whether atrial activation is intrinsic or RA-paced)
pace RV using AVD+VVD
For RV first pacing (i.e. RV pre-excitation) based on atrial events sensed via the P4 electrode where AVD=EMOTE-1+:
pace RV using AVD−VVD
pace LV using AVD The calibration procedure can be repeated periodically or as needed to update the EMOTE values. Between recalibration procedures, the implanted device can adjust the current set of EMOTE values based on changes, if any, in the intraatrial conduction delay (RA-LA) of the patient. In one particular example, if RA-LA is found to have increased by 10%, the various EMOTE values can be likewise increased by 10%.

In a second set of exemplary embodiments, no external reference system is used to calibrate the procedure. Rather, the implanted device employs an implantable detector to detect the LA cardiomechanical activation. The implantable detector can, for example, employ cardiogenic impedance detection using the P4 electrode to identify an estimate of biatrial volumes or of mitral annular motion times. Heart sounds can also be detected using a suitable sensor to identify S1 early onset or a mitral valve closure. In either case, the detection of an LA cardioelectric event via the P4 electrode is used to trigger the beginning of a search window for detecting LA cardiomechanical activation (via cardiogenic impedance, sound-based systems or other suitable techniques.) Based on the timing of LA pace and sense events detected via the P4 electrode and the subsequent LA cardiomechanical activation detected using the implanted sensor, the implantable device determines a set of electromechanical delay values referred to herein as Electro-Mechanical Offset Actual Time (EMOAT) values, which are then used to set AV delays to optimal values. QuickOpt™ techniques or other suitable optimization techniques are used to set VVD to optimal values and to determine whether the RV or LV should be paced first.

In one particular EMOAT example, the set of values that are determined include: an EMOAT-1i value representing a time delay from an intrinsic LA depolarization as sensed at P4 to the LA cardiomechanical activation as detected using the implanted sensor; an EMOAT-2i value representing a time delay from an intrinsic RA depolarization as sensed at P4 to the LA cardiomechanical activation as detected using the implanted sensor; an EMOAT-1r value representing a time delay from an RA-paced LA depolarization to the LA cardiomechanical activation as detected using the implanted sensor; and an EMOAT-2r value representing a time delay from an RA pace to the LA cardiomechanical activation as detected using the implanted sensor.

If the implanted device is equipped to use the RA electrode to detect atrial events via an RA sensing channel during biventricular pacing, the device is programmed to use the EMOAT-2 values for setting the AVD. In one particular example, AVD is set equal to EMOAT-2+, where EMOAT-2+ is derived from the EMOAT-2 values based on whether the atrial event is paced or sensed. More specifically, EMOAT-2+ is set equal to EMOAT2i plus a programmable offset for use with intrinsic atrial events sensed in the RA. EMOAT-2+ is instead set equal to EMOAT2r plus the offset for use with paced atrial events. The offset can again be programmed to 20 ms for sensed events and 30 ms for paced events, adjustable based on heart rate, patient posture and/or activity. Having set the value for AVD to EMOAT-2+ for use with RA sensing, the device then controls biventricular pacing based on atrial events sensed using the RA lead by applying the AVD and VVD values to atrial pace/sense times as follows:

For LV first pacing (i.e. LV pre-excitation) based on atrial events sensed via the RA lead where AVD=EMOAT-2+:
  pace the LV using AVD (e.g. add AVD to the time of RA depolarization as sensed or paced using the RA lead)
  pace RV using AVD+VVD
For RV first pacing (i.e. RV pre-excitation) based on atrial events sensed via the RA lead where AVD=EMOAT-2+:
  pace RV using AVD−VVD
  pace LV using AVD If the implanted device is instead equipped to use the P4 electrode to detect atrial events via a separate P4 sensing channel during biventricular pacing, the device is instead programmed to use the EMOAT-1 values for setting the AVD. In one particular example, AVD is set equal to EMOAT-1+, where EMOAT-1+ is set equal to EMOAT1i plus a programmable offset for use with intrinsic atrial events sensed in the LA via P4 and is instead set equal to EMOAT1r plus the offset for use with paced atrial events. Having set the AVD to EMOAT-1+ for use with P4 sensing, the device then controls biventricular pacing based on atrial events sensed using P4 by applying the AVD and VVD values as follows:

For LV first pacing (i.e. LV pre-excitation) based on atrial events sensed via the P4 electrode where AVD=EMOAT-1+:
  pace the LV using AVD (e.g. add AVD to the time of LA depolarization as sensed using the P4 lead while accounting for whether atrial activation is intrinsic or RA-paced)
  pace RV using AVD+VVD
For RV first pacing (i.e. RV pre-excitation) based on atrial events sensed via the P4 electrode where AVD=EMOAT-1+:
  pace RV using AVD−VVD
  pace LV using AVD System and method implementations of these and other techniques are presented herein. Although summarized primarily with respect to implementations having a quad-pole LV lead, aspects of the invention are also generally applicable to systems having other multi-pole LV leads and to systems having multi-pole RV leads or RA leads.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Systems and Methods

Figure 1:
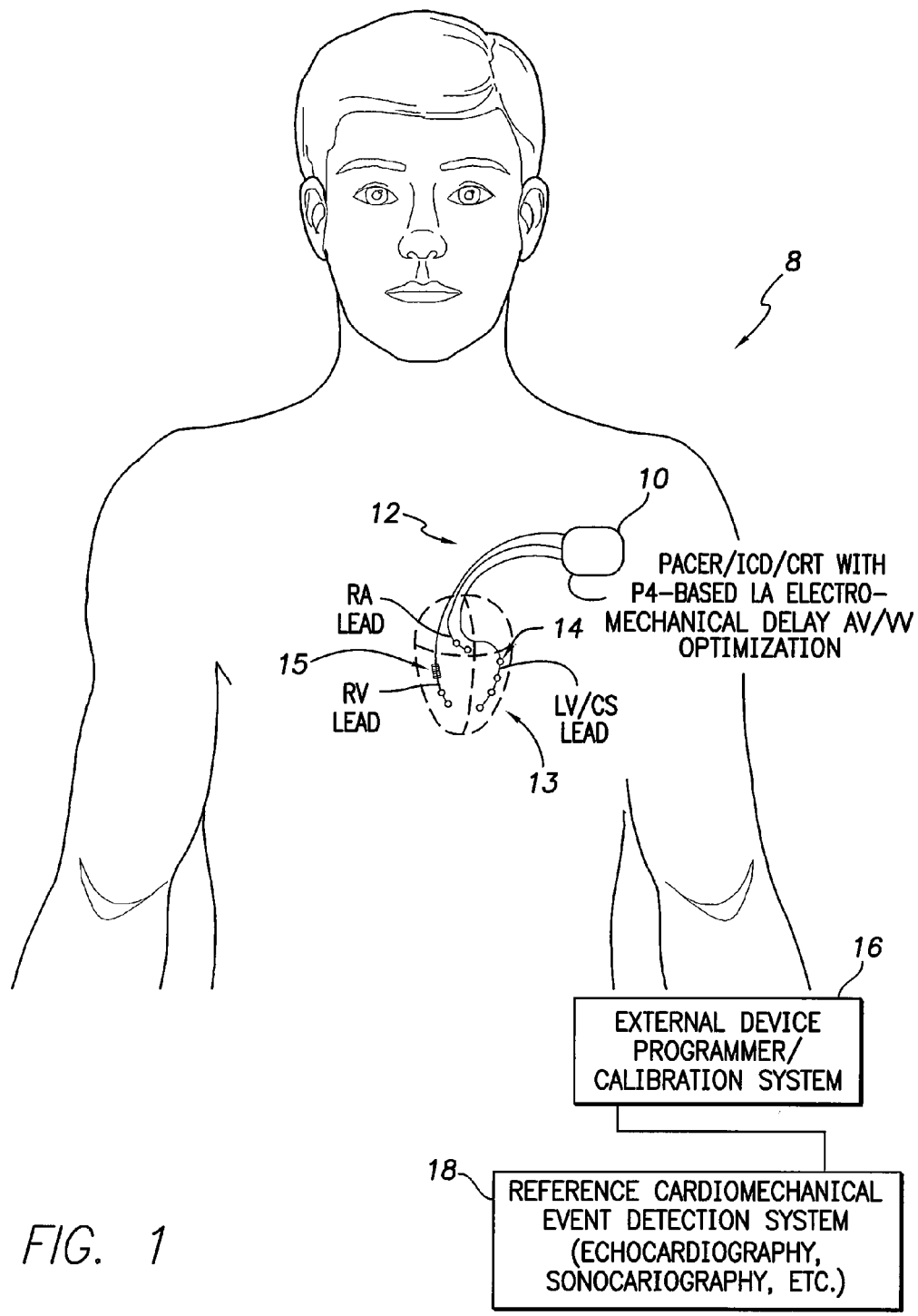
FIG. 1 illustrates components of an implantable medical system having a pacemaker, ICD or CRT device capable of optimizing biventricular AV/VV pacing delays based on P4-based LA electromechanical delays.

FIG. 1 illustrates an implantable medical system 8 capable of optimizing biventricular AV/VV pacing delays (alone or in conjunction with external systems) based on LA electromechanical delays for use with CRT. In this example, the implantable medical system 8 includes a pacer/ICD/CRT 10 or other cardiac stimulation device (such as a CRT-D) equipped with a set of cardiac sensing/pacing leads 12 implanted on or within the heart of the patient, including a multi-pole LV lead implanted via the coronary sinus (CS). In FIG. 1, a stylized representation of the set of leads is provided. More accurate illustrations of the leads are provided within the other figures. To illustrate the multi-pole configuration of the LV lead, a set of electrodes 13 is shown distributed along the LV lead, including a proximal electrode (P4) 14 implanted in or near an AV groove of the heart for sensing LA activation. In the examples described herein, a quad-pole (or "quadrapolar" or "quadripolar") lead is employed (such as the Quartet™ lead provided by St Jude Medical.) Other suitable leads may instead be employed, including leads with more or fewer electrodes. Also, as shown, an exemplary RV lead is provided that includes an RV tip/ring electrode pair and an RV coil 15. An RA lead is also provided that includes an RA tip/ring pair. Other electrodes of various sizes and shapes may be additionally or alternatively provided, such as coil electrodes mounted in or on the RA or in the CS. Although identified as a pacer/ICD/CRT in FIG. 1, it should be understood that device 10 can be any suitably-equipped implantable medical device, such as a standalone pacemaker, ICD, or CRT device, including CRT-D and CRT-P devices. In the following, for brevity, device 10 will be referred to simply as a pacer/CRT.

In some implementations, the pacer/CRT itself performs the AV/VV optimization based on electrocardiac signals sensed using its leads and cardiomechanical signals sensed via suitable implanted detectors (not specifically shown in FIG. 1.) In other implementations, the device transmits pertinent electrocardiac parameters to an external device programmer 16, which performs the optimization in conjunction with cardiomechanical signals received from an external cardiomechanical event detection system 18 (such as a reference system exploiting echocardiography, sonocardiography, etc.) That is, the external programmer calibrates EMOTE values for use with the patient, which are then programmed into the pacer/CRT via telemetry under clinician supervision. Note that other external systems might instead be used to perform the calibration, such as bedside monitors or the like. In some embodiments, the external system is directly networked with a centralized computing system, such as the HouseCall™ system or the Merlin@home/Merlin.Net systems of St. Jude Medical, which can perform at least some of the processing.

Figure 2:
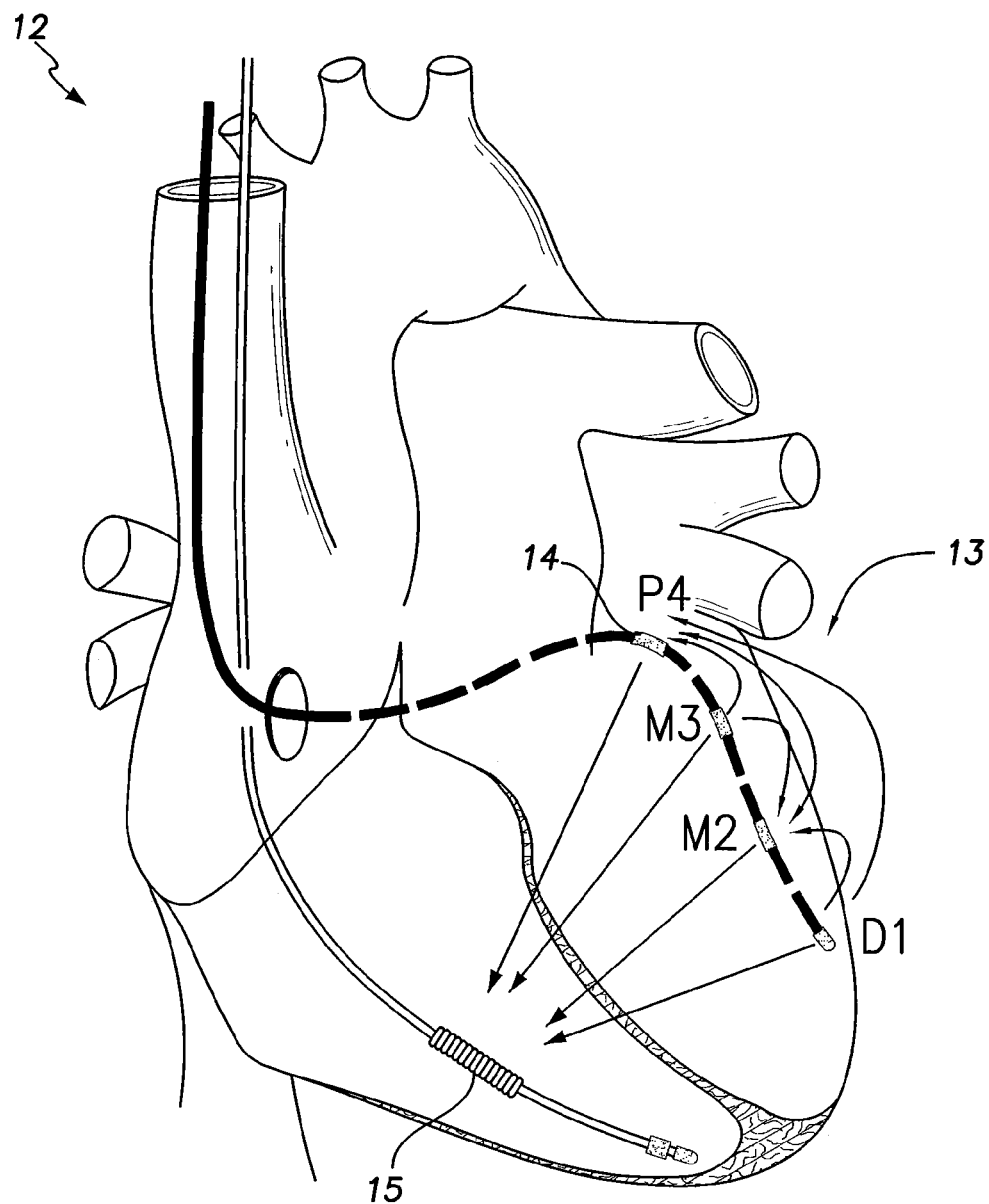
FIG. 2 illustrates a multi-polar LV lead and its implant location for use with the system of FIG. 1.

FIG. 2 provides another stylized illustration of the heart of the patient showing the RA and LV leads of lead system 12 in greater detail and, in particular, showing the four LV electrodes of the exemplary quad-pole LV lead, which are denoted, from distal LV to proximal LV as: D1, M2, M3, and P4. As already noted, the P4 electrode is implanted in or near the AV groove for use in assessing LA activation. The figure also shows various sensing vectors between the LV electrodes and coil electrode 15 of the RV lead and also illustrates various interelectrode sensing vectors among the electrodes of the LV lead. The purpose of the various sensing vectors will be discussed below in connection with the detailed descriptions of various exemplary embodiments.

With quad-pole leads such as the Quartet™ lead, the P4 proximal electrode lies in or near the AV groove in a majority of patients. Even if it lies fully over LV tissue, it is almost always sufficiently close to the AV groove and LA so that unipolar signals will show A potentials as well as V potentials. Insofar as the location of the AV groove is concerned, the atria of the heart are separated from the ventricles by the coronary sulcus (also called the coronary groove, auriculoventricular groove or AV groove.) More specifically, the coronary sulcus is a surface groove encircling the heart that separates the atria from the ventricles. It contains the right coronary artery, the small cardiac vein, the coronary sinus, and the circumflex branch of the left coronary artery. Herein, the term "AV groove" is deemed to be generally equivalent to "coronary sulcus", "coronary groove" or "auriculoventricular groove."

Note that the particular locations of the implanted components shown in FIGS. 1 and 2 are merely illustrative and may not necessarily correspond to actual implant locations. Also, although the descriptions herein use the Quartet™ lead as an exemplary component of the invention, it should be understood that any suitable LV lead could instead be used so long as it has at least one suitable electrode implanted in or near the AV groove for sensing LA activation.

Figure 3:
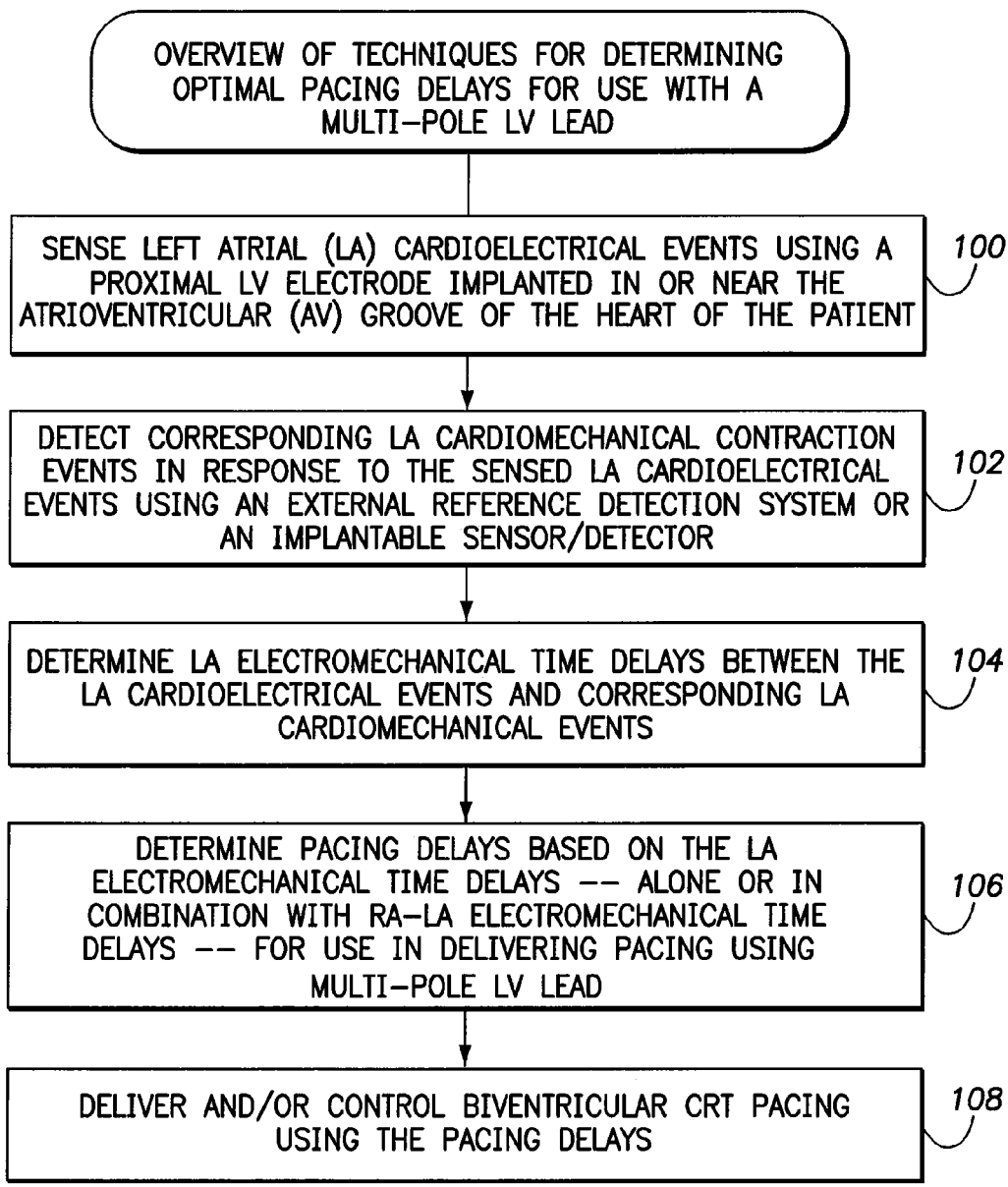
FIG. 3 summarizes a general technique for determining preferred or optimal biventricular pacing delays based on P4-based LA electromechanical delays that may be performed by the system of FIGS. 1 and 2.

FIG. 3 broadly summarizes the techniques exploited by the pacer/CRT of FIG. 1 (or other suitably-equipped systems) for determining optimal pacing delays, alone or in combination with external calibration systems. Beginning at step 100, an LA cardioelectrical event is sensed by the implanted device using the proximal LV electrode (P4), which is implanted in or near the AV groove of the heart of the patient. For example, the P4-RVcoil vector may be used to sense LA depolarization signals within a P4-RVcoil IEGM. At step 102, a corresponding LA cardiomechanical event is detected that is responsive to (i.e. triggered by) the cardioelectrical event, such as an event representative of LA contraction. The LA cardiomechanical event may be detected using one of the aforementioned external reference detection systems, such as an echocardiographic system or a sonocardiographic system, or by using an implantable detector, such as a cardiogenic impedance detector, heart sound detector or accelerometer, assuming the implantable system is so equipped. At step 104, the LA electromechanical time delay between the LA cardioelectrical event and the LA cardiomechanical event is determined and then, at step 106, pacing delays are determined or set based on the LA electromechanical time delays—alone or in combination with RA-LA electromechanical time delays obtained using an RA electrode—for use in delivering pacing using the multi-pole LV lead, alone or in combination with other leads. The pacing delays may include AV delays, as well as VV delays, for use with biventricular CRT pacing. Finally, at step 108, the implanted device delivers and/or controls pacing using the pacing delays, such as biventricular or multisite LV (MSLV) CRT.

CRT and related therapies are discussed in, for example, U.S. Pat. No. 6,643,546 to Mathis, et al. entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing". See, also, U.S. Patent Application No. 2008/0306567 of Park et al., entitled "System and Method for Improving CRT Response and Identifying Potential Non-Responders to CRT Therapy" and U.S. Patent Application No. 2007/0179390 of Schecter, entitled "Global Cardiac Performance."

Hence, systems and methods are provided for CRT programming guidance based on left heart interval optimization. By utilizing a quad-pole lead with a proximal electrode near the AV groove, LA electrical activation can be sensed from the implanted device/lead system. A calibration procedure performed at least once near the time of implant, and optionally repeated at regular intervals or after some level of reverse remodeling has occurred, sets the LA electromechanical time, which is the time between LA sensed electrical event and LA mechanical event (preferably completion of atrial kick and/or closure of the mitral valve). AV and/or VV delays are adjusted based on this LA electromechanical time, thereby allowing delivery of the LV pacing pulse at a time of optimal left heart filling. Additional sensors integrated in the device can be used for a calibration procedure or for real-time ongoing monitoring of LA electromechanical time and interval adjustment. These techniques will now be described in more detail with reference to various exemplary embodiments.

Exemplary EMOTE Techniques for Use with External Calibration

FIGS. 4-9 illustrate various examples where an external reference system is employed to estimate electro-mechanical offset times for use in programming the pacer/CRT, i.e. the techniques exploit various EMOTE values. In a first example (FIGS. 4-6), the EMOTE values are programmed into a pacer/CRT that, during subsequent biventricular pacing, employs an RA sensing channel to sense LA electrical activation using, e.g., RA tip/ring electrodes. As such, the sensing channel detects LA activation via the RA and so the pacer/CRT uses EMOTE-2 values, which are specifically calibrated for use with RA channel sensing. In a second example, (FIGS. 7-9), the EMOTE values are programmed into a pacer/CRT that, during subsequent biventricular pacing, employs a separate sensing channel coupled to the P4 electrode to sense the LA electrical activation (such as P4-RAring channel). As such, the sensing channel detects LA activation via P4 and so the pacer/CRT uses EMOTE-1 values, which are specifically calibrated for use with P4 channel sensing.

The choice between using a P4 sensing channel (along with the EMOTE-1 values) as opposed to using the RA sensing channel (along with the EMOTE-2 values) depends on various factors. For example, the device manufacturer might choose a particular embodiment (P4 vs. RA) based on available hardware, including the number of available sense channels. (In circumstances where there are not enough sensing channels to accommodate P4 sensing during actual CRT pacing, the device can be programmed during calibration to devote a sensing channel to P4 for the purposes of collecting calibration data. Once calibration is complete, the sensing channel can then be reprogrammed to another sensing vector—such as a bipolar RA vector—for use in controlling CRT pacing.) Assuming, though, that the device offers a choice between P4 and RA, the implanting physician can decide based on which LV lead is used and where the P4 electrode is situated (and in particular on whether there is a sufficiently large and clear LA signal on the P4 IEGM.) The choice might also be made based on a priori knowledge of underlying atrial conduction. For example, if the patient is known to have substantial and variable biatrial conduction delay, the P4 embodiment is preferred; whereas if the patient has relatively normal biatrial conduction, then the RA embodiment would suffice.

The first EMOTE example (which is employed with a pacer/CRT programmed to use an RA sense channel during CRT to sense atrial electrical events) will now be described in detail with reference to FIG. 4. Briefly, in conjunction with a CRT system (such as a Promote Quadra™ pulse generator, Tendril™ RA pacing lead, Durata™ RV ICD lead, and a Quartet™ LV lead), the proximal (P4) electrode of the LV lead is used for LA sensing. Using new or existing detection techniques or algorithms, the time of LA activation as recorded by the P4-Case, P4-RV Coil, P4-RA Ring, or P4-any LV electrode sense vector is noted as being representative of the LA electrical activation event. Sensing vectors that record far-field LA activation can also be used to detect left activation time. In this case, LA timing can be annotated from either the peak or the end (i.e., the return to the baseline) of far-field left atrial activation in the ventricular intracardiac electrogram.

Figure 4:
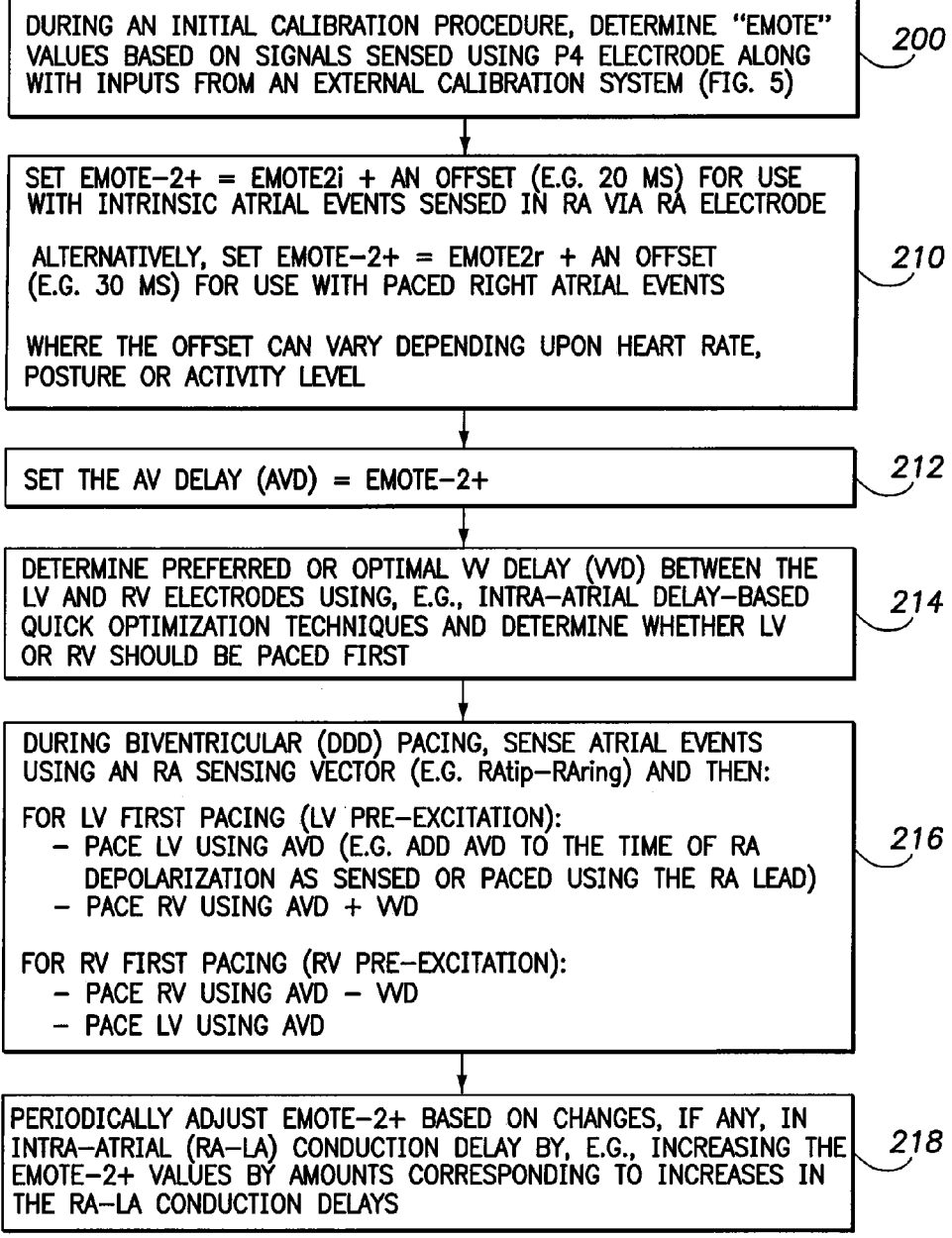
FIG. 4 is a flowchart illustrating a first exemplary EMOTE implementation of the method of FIG. 3 wherein an external reference technique is employed to detect LA cardiomechanical delays for use in setting AV values for use with atrial events detected via an RA sensing channel of the device.

Beginning at step 200 of FIG. 4, during the initial calibration procedure, an external calibration system in communication with the pacer/CRT determines EMOTE values based on signals sensed by the pacer/CRT using the P4 electrode along with inputs from an external calibration system. The details of the calibration procedure are provided within FIGS. 5 and 6. This electromechanical time calibration procedure is preferably performed at least at, or shortly after, the time of device implantation. Briefly, the calibration procedure consists of streaming a P4 sense channel signal in conjunction with a reference method for LA mechanical activation. That is, at step 202 of FIG. 5, during the calibration procedure, the external calibration system detects LA cardiomechanical activation using a reference detection technique (such as echocardiography, discussed below.) Concurrently, at step 204, the pacer/CRT detects various intrinsic and paced atrial events using a sensing vector incorporating an AV groove electrode, such as the P4-RAring sensing vector. Other suitable P4 sensing vectors include: P4-Case, P4-RVcoil, P4-M2, P4-M3 and P4-D1 (i.e. P4 in combination with any of the other LV electrodes.)

More specifically, at step 204, the time of LA electrical activation as recorded by any of these sensing vectors is noted as being representative of the LA electrical activation event. Either the peak of the depolarization event within the IEGM or the end of the depolarization event (i.e. the return to baseline) can be used so long as consistency is maintained. As noted, sensing vectors that record far-field LA activation can also be used to detect the LA activation time. In this case, LA timing can be annotated from either the peak or the end of far-field LA activation in a ventricular intracardiac electrogram (V-IEGM). Insofar as "detecting" paced events, the device records the time at which atrial pacing pulses are delivered to the RA and/or LA and also detects the peak (and/or end) of the resulting paced depolarization in the opposing atrial chamber.

Figure 5:
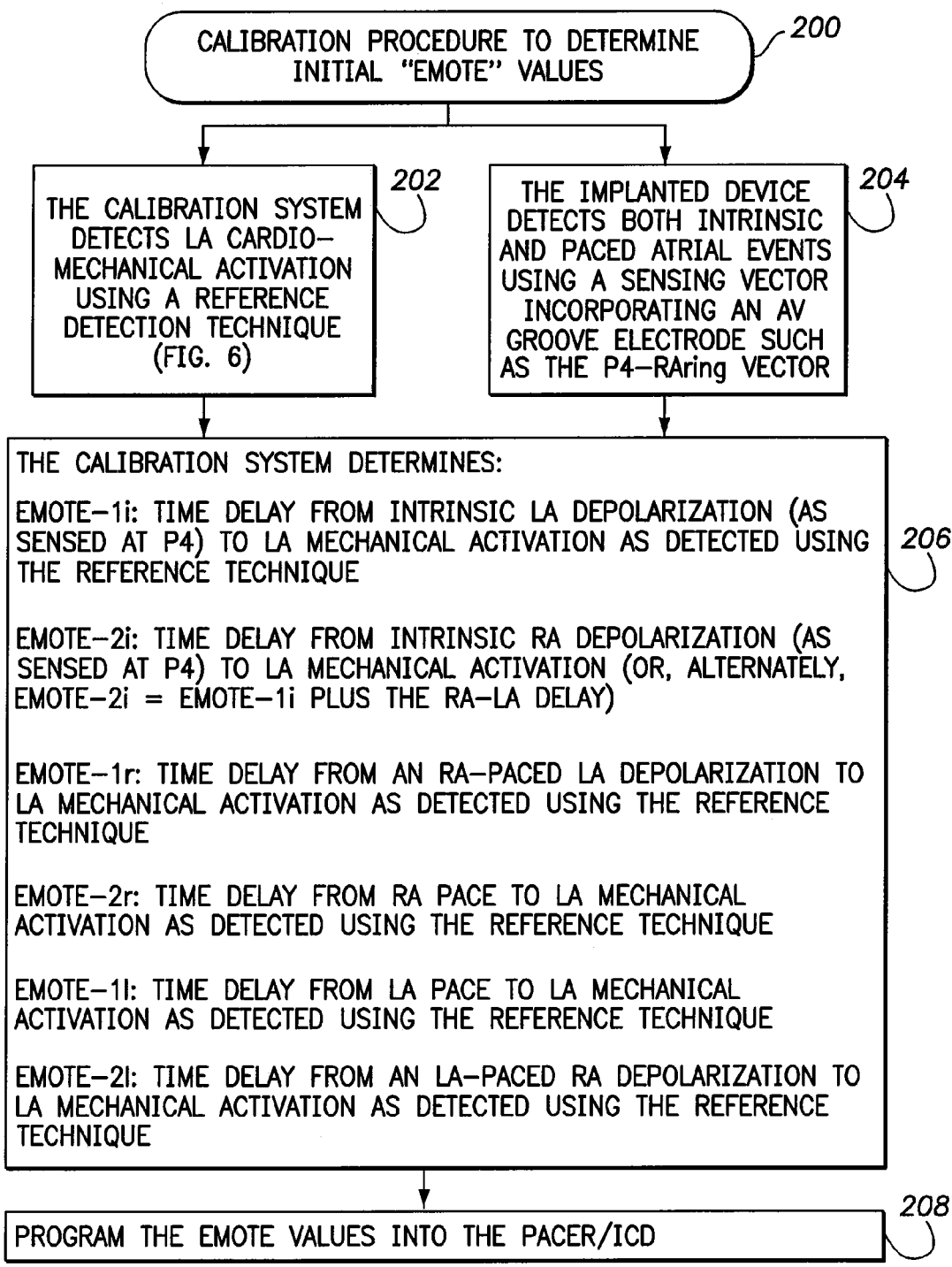
FIG. 5 is a flowchart illustrating exemplary calibration techniques for determining EMOTE values for use with the technique of FIG. 4.

At step 206 of FIG. 5, the calibration system determines:
EMOTE-1i: the time delay from an intrinsic LA depolarization (as sensed using P4) to LA cardiomechanical activation as detected using the reference technique;
EMOTE-2i: the time delay from an intrinsic RA depolarization (as sensed using P4) to LA cardiomechanical activation (or, alternately, EMOTE-2i=EMOTE-1i+ the RA-LA delay, as detected by the pacer/CRT);
EMOTE-1r: the time delay from an RA-paced LA depolarization to LA cardiomechanical activation as detected using the reference technique (where an RA-paced LA depolarization is a depolarization event in the LA triggered by a pacing pulse delivered to the RA);
EMOTE-2r: the time delay from RA pace to LA cardiomechanical activation as detected using the reference technique (where "RA pace" refers to the time at which a pacing pulse is delivered to the RA);

EMOTE-1l: the time delay from LA pace to LA cardiomechanical activation as detected using the reference technique (where "LA pace" refers to the time at which a pacing pulse is delivered to the LA);

EMOTE-2l: the time delay from an LA-paced RA depolarization to LA cardiomechanical activation as detected using the reference technique (where an LA-paced RA depolarization is a depolarization event in the RA triggered by a pacing pulse delivered to the LA.)

That is, EMOTE-1i can be defined as the time from LA IEGM sense (on the P4 electrode) to the mechanical activation by one of the above methods. EMOTE-2i can be defined as the time from RA IEGM sense to the LA mechanical activation; or alternately, EMOTE-1i plus RA-LA electrical delay. In like manner, the EMOTE-2 values are recorded based on RA activation using the time from RA sense or pace to LA sense and the time from LA sense to LA mechanical activation. Note that EMOTE-1 will almost always be shorter than EMOTE-2, since RA typically activates in response to sinoatrial node depolarization while LA requires activation to travel across Bachmann's bundle or across atrial myocardium. Insofar as EMOTE-1l and EMOTE-2l, these values represent the electromechanical offset time estimate during LA pacing, which can be obtained by pacing the P4 electrode and confirming LA capture. It should be noted that EMOTE-2l can be determined and recorded but it is not necessarily a useful quantity for optimizing LV filling in most patients, since while pacing the LA, the LA activation and electromechanical time will inherently be more related to the time of LA pace than to RA sense. However, for patients with right heart failure, pulmonary hypertension, right bundle branch block (RBBB), or other abnormalities that would better be corrected by optimizing RV filling instead of LV filling, EMOTE-2l might be useful. The principles guiding such right side optimization will be apparent to those skilled in the art based on the left side optimization techniques described herein in detail.

At step 208, the EMOTE values are programmed into the pacer/CRT so that the values can then be used to set the AV delays. In this particular example, since the device is equipped to use the RA sensing channel during CRT, it is only necessary that the EMOTE-2 values be programmed into the device (though both EMOTE-1 and EMOTE-2 values can be programmed.)

Returning to FIG. 4, at step 210, the pacer/CRT uses the EMOTE-2 values determine during calibration to set EMOTE-2+ values, which include an offset. More specifically, the pacer/CRT sets:

EMOTE-2+=EMOTE2i+an offset (e.g. 20 ms) for use with intrinsic atrial events sensed in RA via RA electrode; and EMOTE-2+=EMOTE2r+an offset (e.g. 30 ms) for use with paced atrial event where the offset is selected so as to achieve maximum LV output by, e.g., timing ventricular pacing to coincide with a time of maximum LV filling. The offset can vary depending upon the current heart rate, patient posture and current activity level or other factors. That is, the device may be equipped to detect posture and activity and to adjust the offset values based on posture and/or activity. For example, the device can store several different EMOTE intervals based on posture and activity level (among other factors.) The device utilizes the appropriate EMOTE values based on position and activity level in real-time as determined, e.g., by an on-board accelerometer.

Techniques for detecting posture are discussed in, for example, U.S. Pat. No. 7,149,579 of Koh et al., entitled "System and Method for Determining Patient Posture based on 3-D Trajectory using an Implantable Medical Device." Techniques for assessing patient activity are discussed in, for example, U.S. Pat. No. 7,054,687 of Andersen, "Method and Apparatus for Position and Motion Sensing." Adjustment to the offset values based on posture and/or activity may be made based on predetermined adjustment values stored within the device. For example, data may be collected for the patient during calibration while the patient is in different postures or undergoing different levels of activity so that the adjustments may be determined sufficient to improve or maximize cardiac output. Also, it should be understood that different offset values might be defined for use with intrinsic events as opposed to paced events. Likewise, different offsets may be defined for use with EMOTE-2 values as opposed to EMOTE-1 values. The offset values of 20 ms for use with sensed events and 30 ms for use with paced events are merely exemplary. Otherwise routine experimentation can be used to determine preferred or optimal offset values for particular patients or classes of patients.

At step 212, the pacer/CRT then sets the AV delay (AVD) to EMOTE-2+, where, as noted, the value of EMOTE-2+ depends on whether the atrial event is paced or sensed. (Alternatively, the EMOTE-2+ value for use with sensed (i.e. intrinsic) events may be denoted "EMOTE-2i+" and the EMOTE-2+ value for use with paced events may be denoted "EMOTE-2r+".)

At step 214, the pacer/CRT then determines a preferred or optimal VV delay (VVD) between the LV and RV electrodes using, e.g., inter-ventricular delay-based quick optimization techniques (QuickOpt™) and determines whether the LV or the RV should be paced first (i.e. LV pre-excitation vs. RV pre-excitation.) QuickOpt™ techniques are discussed in the above-cited patent to Bruhns et al. and in at least some of the following patent documents: U.S. Patent Published Application No. 2005/0125041, entitled "Methods for Ventricular Pacing"; U.S. patent application Ser. No. 10/974,123, filed Oct. 26, 2004; U.S. Pat. No. 7,590,446; U.S. patent application Ser. No. 10/980,140, filed Nov. 1, 2004; U.S. patent application Ser. No. 11/129,540, filed May 13, 2005; U.S. patent application Ser. No. 11/952,743, filed Dec. 7, 2007. See, also, U.S. Published Patent Application No. 2010/0145405, entitled "Systems and Methods for Controlling Ventricular Pacing in Patients with Long Intra-Atrial Conduction Delays", U.S. Published Patent Application No. 2009/0299423, entitled "Systems and Methods for determining Intra-Atrial Conduction Delays using Multi-Pole Left Ventricular Pacing/Sensing Leads", and U.S. Published Patent Application No. 2011/0022106, entitled "Systems and Methods for Optimizing Ventricular Pacing Delays During Atrial Fibrillation."

Alternatively, the determination of whether LV or RV should be paced first can be based on whether the patient has left bundle branch block (LBBB) or RBBB conduction abnormalities. That is, the clinician identifies these abnormalities within the patient and then programs the pacer/CRT with that information for use in selecting between LV pre-excitation and RV pre-excitation.

At step 216, the pacer/CRT delivers and/or controls biventricular DDD pacing using the AVD and VVD values. (DDD refers to Dual pacing for both chambers, Dual chamber activity sensing, and Dual response (i.e. triggering and inhibition.)) More specifically, at step 216, the device senses atrial events using an RA sensing vector, and/or paces the RA, and then:

for LV first pacing (LV pre-excitation):
  pace LV using AVD (e.g. the device adds AVD to the time of RA depolarization as sensed or paced using the RA lead)
  pace RV using AVD+VVD
for RV first pacing (RV pre-excitation):
  pace RV using AVD−VVD
  pace LV using AVD.

The RA sensing vector that is used is typically a bipolar RA tip-ring vector, as that usually gives the sharpest and clearest delineation of local activation. However, a unipolar RA sensing vector (i.e. RAtip-case) can instead be used so long as appropriate sensing and activation detection algorithms are implemented. In this regard, bipolar sensing typically chooses the absolute peak within the IEGM—positive or negative (whichever is larger)—whereas unipolar sensing typically chooses the steepest descent (i.e. the peak negative derivative: −dV/dt max.)

Note that it is advantageous to allow re-calibration of the EMOTE intervals at in-clinic follow-up procedures. However, it is possible to estimate EMOTE-2 from any changes in RA-LA conduction delay detected by RA and LA IEGMs without re-calibration. Accordingly, at step 218, the pacer/CRT periodically adjusts the EMOTE-2+ values based on changes, if any, in inter-atrial (RA-LA) conduction delay by, e.g., increasing the EMOTE-2+ values by amounts corresponding to increases in the RA-LA conduction delays. In one example, if RA-LA increases by 10%, the device can increase the EMOTE-2+ values by 10%. More sophisticated adjustment techniques may be employed, as well. Also, in addition to any device-based adjustments, the entire calibration procedure can be repeated by having the patient return to the clinician to update the EMOTE values. The calibration procedure can be repeated periodically or on-demand (as might be initiated by the clinician in view of any significant progression or regression of heart disease within the patient.)

Figure 6:
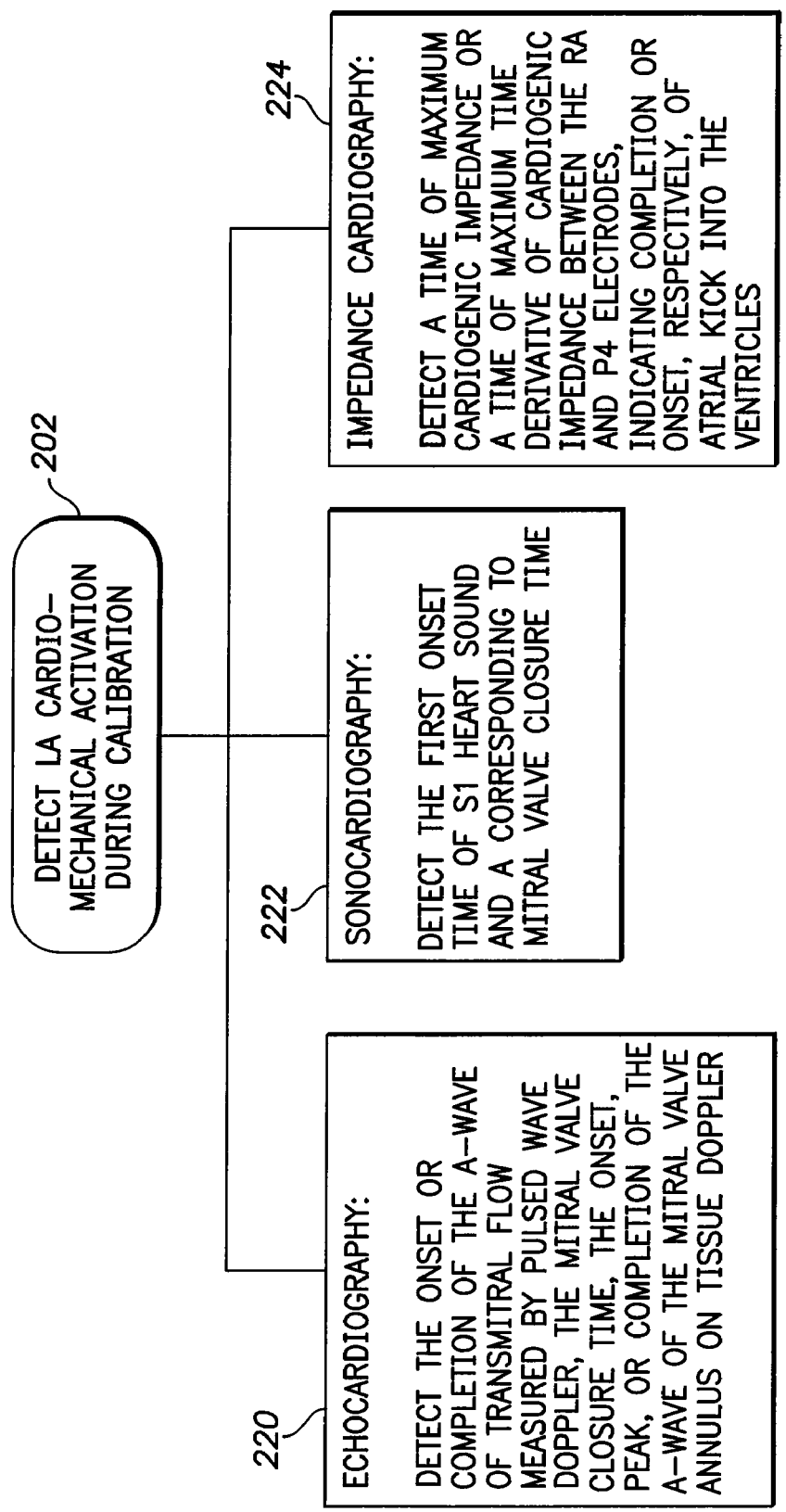
FIG. 6 is a flowchart illustrating exemplary reference techniques for detecting LA cardiomechanical contraction for use with the technique of FIG. 5.

With reference to FIG. 6, techniques for detecting LA cardiomechanical activation during calibration will now be described further. Any of a variety of reference techniques may be exploited, alone or in combination, during calibration to detect LA cardiomechanical activation (i.e. the mechanical contraction of the LA.) The reference techniques described herein include echocardiography, sonocardiography (sometimes referred to as phonocardiography) and impedance cardiography. Echocardiography is a diagnostic test that uses ultrasound to create images of heart chambers, valves and surrounding structures and can be used to measure cardiac output. Sonocardiography/phonocardiography is typically a non-invasive technique used to amplify faint, low frequency sounds of blood flowing through the heart and great vessels and is often performed in synchrony with ECG/EKG and echocardiography to match heart sounds with the point at which they occur in the heartbeat. Impedance cardiography is a type of impedance plethysmography wherein impedance is measured between electrodes positioned around the neck and lower thorax. Impedance cardiography is typically used to calculate stroke volume and cardiac volume but can also be used to assess myocardial contractility, thoracic fluid content and circulation. It should be noted that sonocardiography can optionally be performed by device-based 3D accelerometers or microphones, and cardiogenic impedance can optionally be performed by device-based impedance measurement circuitry.

At step 220 of FIG. 6, echocardiography is performed to detect the onset or completion of the A-wave of transmitral flow as measured, e.g., by Pulsed Wave Doppler. In another example, the echocardiography system can detect the mitral valve closure time and/or the onset, peak, or completion of the A-wave of the mitral valve annulus, as detected via Tissue Doppler. Additionally or alternatively, at step 222, sonocardiography/phonocardiography is performed to detect the first onset time of S1 heart sound and a corresponding to mitral valve closure time. In yet another alternative, at step 224, impedance cardiography is performed to detect a time of maximum cardiogenic impedance or a time of maximum time derivative of cardiogenic impedance between the RA and P4 electrodes, indicating completion or onset, respectively, of atrial kick into the ventricles. Typically, only one of these three main reference techniques is performed. However, in at least some cases, two or more separate reference techniques may be performed concurrently and the results combined to provide greater reliability.

Figure 7:
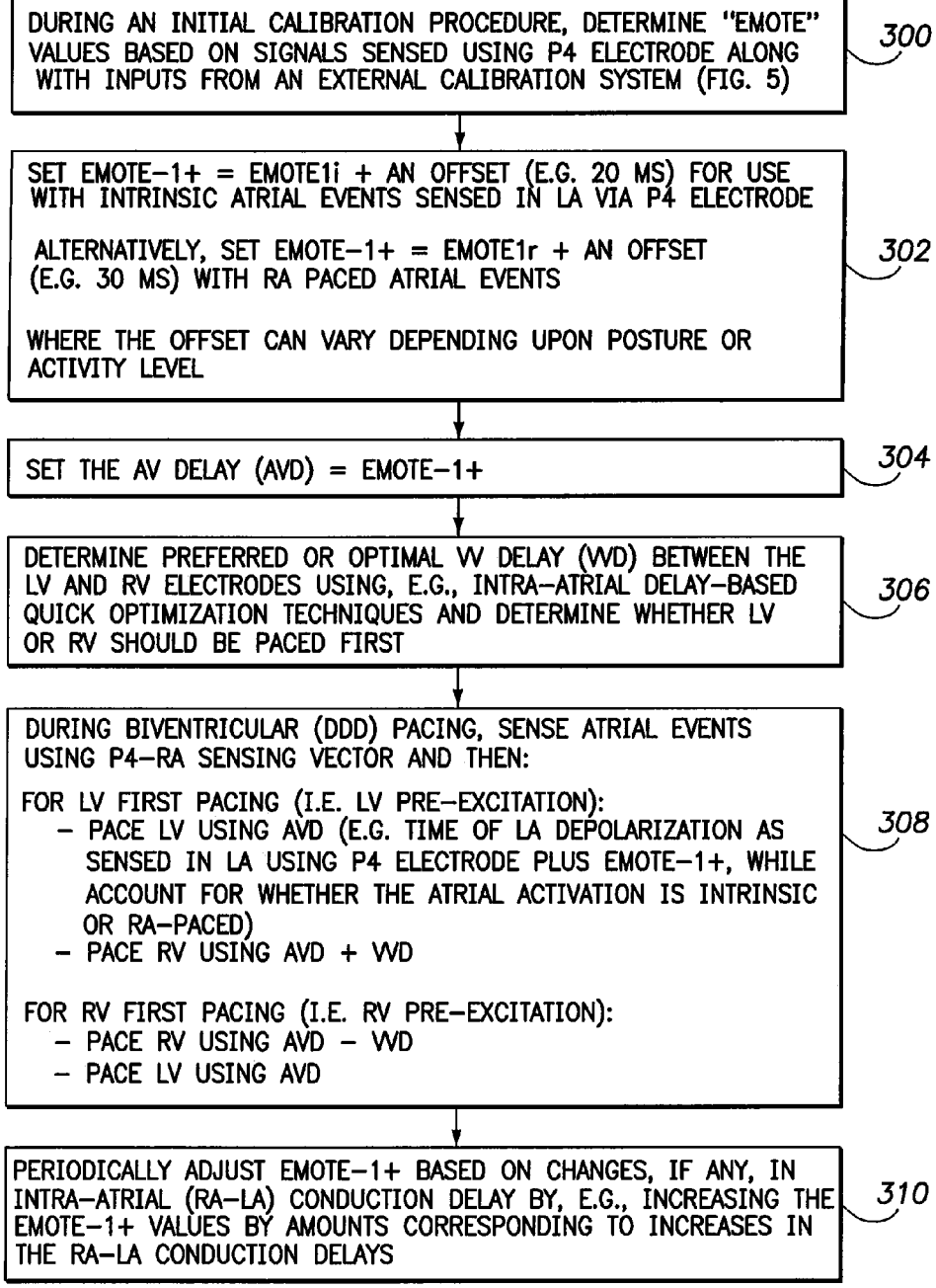
FIG. 7 is a flowchart illustrating a second exemplary EMOTE implementation of the method of FIG. 3 wherein an external reference technique is used to calibrate AV values for use with atrial events detected via a P4 sensing channel.

Turning now to FIGS. 7 and 8, the second EMOTE example will now be described (which is employed with a pacer/CRT programmed to use a P4 sense channel during CRT to sense LA electrical events.) Many of the steps are similar to those of the preceding embodiment and hence will not be described again in detail. Briefly, beginning at step 300 of FIG. 7, during the initial calibration procedure, the external calibration system determines the aforementioned EMOTE values using the techniques of FIGS. 5 and 6, already described. At step 302 of FIG. 7, the pacer/CRT uses the EMOTE-1 values determine during calibration to set EMOTE-1+ values. More specifically, the pacer/CRT sets:

EMOTE-1+=EMOTE1i+an offset (e.g. 20 ms) for use with intrinsic atrial events sensed in RA via the P4 electrode; and EMOTE-1+=EMOTE1r+an offset (e.g. 30 ms) for use with paced atrial events.

where the offset can again vary depending upon the current patient posture and current activity level or other factors. As noted, this offset can differ from the offset used for the EMOTE-2 values.

At step 304, the pacer/CRT sets AVD to EMOTE-1+. At step 306, the pacer/CRT determines VVD using suitable optimization techniques such as QuickOpt™ and determines whether the LV or RV should be paced first. At step 308, during DDD pacing, the pacer/CRT senses intrinsic or RA-paced atrial events using a P4 sensing vector such as P4-RAring and then:

for LV first pacing (LV pre-excitation):
  pace LV using AVD (e.g. the device adds AVD to the time of LA depolarization as sensed using the P4 sensing channel, and accounting for whether atrial activation is intrinsic or RA-paced)
  pace RV using AVD+VVD
for RV first pacing (RV pre-excitation):
  pace RV using AVD−VVD
  pace LV using AVD.

The P4 sensing vector that is used is preferably the P4-RAring vector because of a closer match in size between the P4 (ring) and RA ring electrodes. However, the RA tip (in either a helix or passive fixation configuration) could instead be used. The latter may simply change the relative size or sharpness of the RA versus LA components of the IEGM signal.

At step 310, the pacer/CRT periodically adjusts the EMOTE-1+ values based on changes, if any, in RA-LA conduction delay by, e.g., increasing the EMOTE-2+ values by amounts corresponding to increases in the RA-LA conduction delays. Also, as discussed above, in addition to any device-based adjustments, the entire calibration procedure can be repeated periodically or on-demand.

Figure 8A:
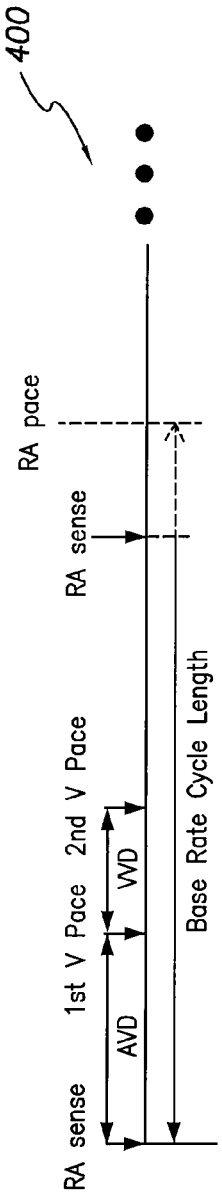
FIGS. 8A-C depict timing diagrams, including prior art diagrams in FIG. 8A and exemplary EMOTE values exploited by the technique of FIG. 7 as shown in FIGS. 8B and 8C.
Figure 8B:
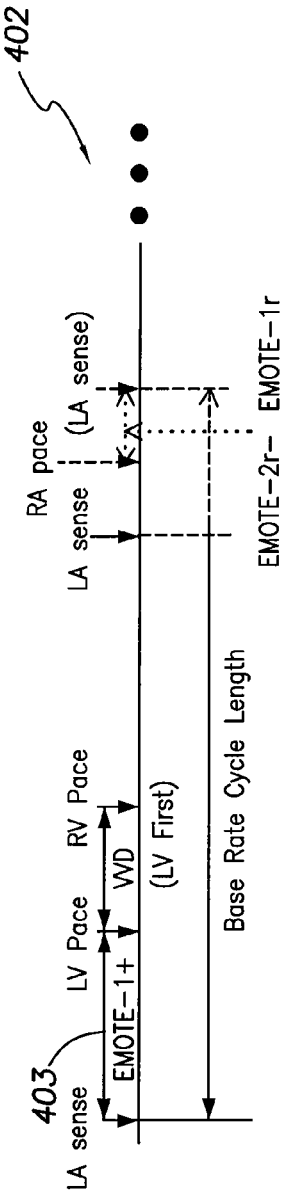
Figure 8C:
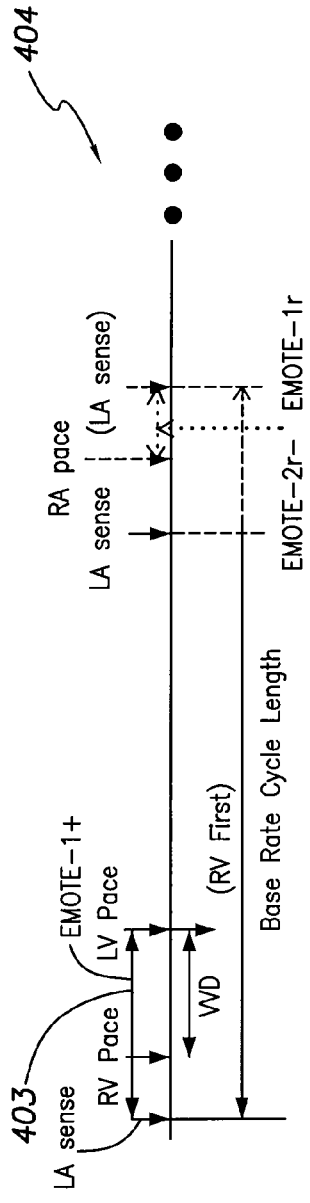

FIGS. 8A-C provide timing diagrams illustrating features of the EMOTE embodiments. A first timing diagram 400 in FIG. 8A illustrates a conventional timing cycle in accordance with prior art techniques wherein AVD and VVD delays are applied following an RA sense. Timing diagram 402 in FIG. 8B shows an EMOTE example wherein the EMOTE-1i delay is applied following an LA sense as detected via a P4 sensing vector in an example of LV-first pacing. Timing diagram 404 in FIG. 8C shows corresponding example of RV-first pacing. As noted, the determination of whether LV or RV should be first is based on conventional VV optimization techniques or on pre-existing knowledge of LBBB or RBBB conduction abnormality. Within the two timing diagrams 402 and 404, the EMOTE-1+ value is specifically shown as time delay 403, which corresponds to AVD and represents the time from an LA sense to delivery of a subsequent ventricular pulse (LV or RV.) As already explained, EMOTE-1+ equals EMOTE-1i plus an offset (for sensed events.)

Figure 9:
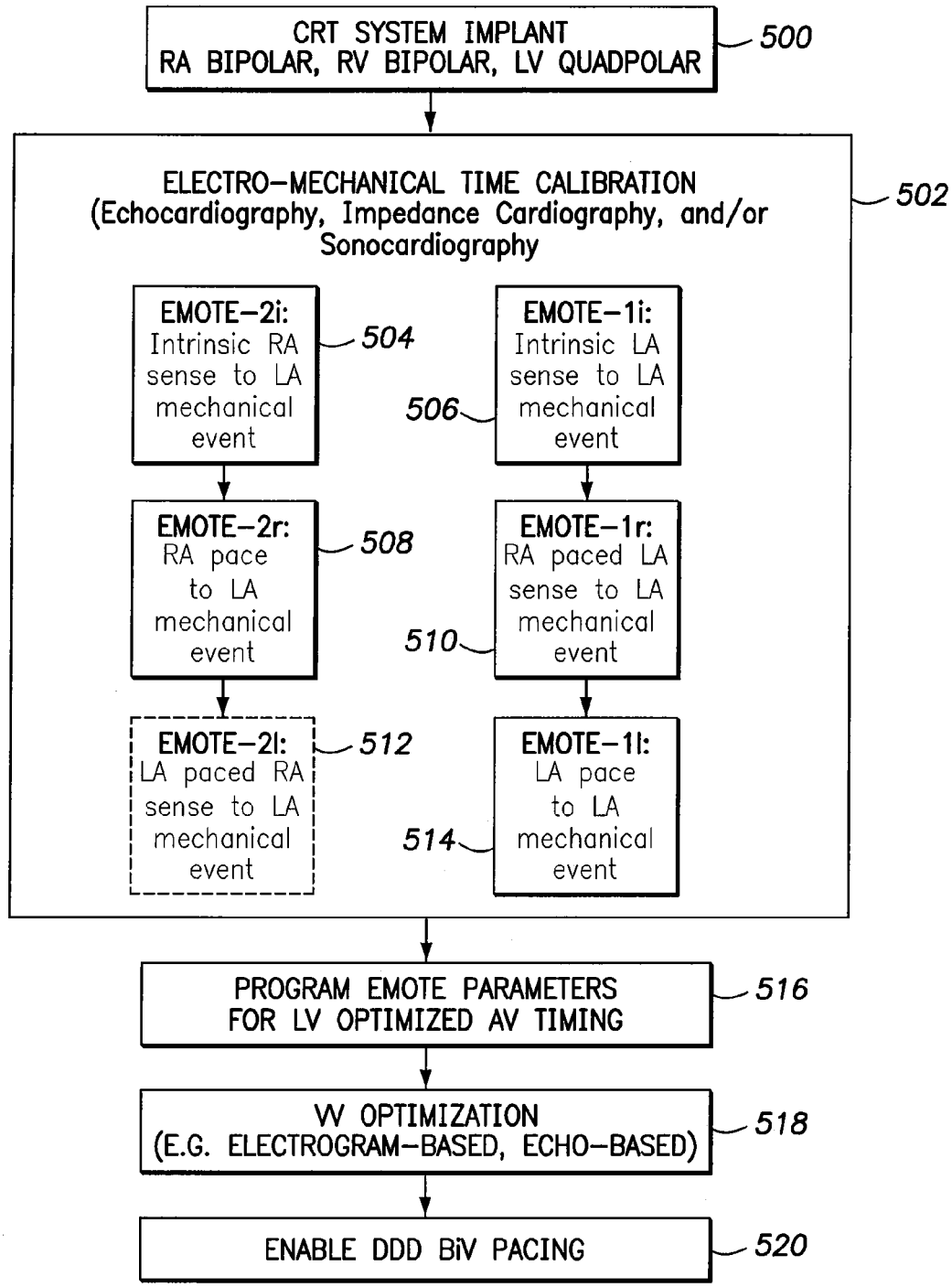
FIG. 9 is a block diagram summarizing the EMOTE techniques of FIGS. 4-8.

FIG. 9 provides an alternative summary of the EMOTE techniques by way of a functional block diagram. Briefly, within block 500, the CRT system (i.e. a pacemaker, ICD or other implantable cardiac rhythm management device equipped for CRT) is implanted within the patient. Thereafter, Electromechanical Time Calibration is performed, within block 502, where the device determines the aforementioned EMOTE values, namely, EMOTE-2i (block 504), EMOTE-1 (block 506), EMOTE-2r (block 508), EMOTE-1r (block 510), EMOTE-2l (block 512), and EMOTE-1i (block 514). The EMOTE-2l block is presented in phantom lines since, as explained above, this value can be determined but is not necessarily as useful as the other parameters in most patients. Within block 516, the EMOTE parameters are programmed into the implantable device for LV optimized AV timing. VV optimization is performed within block 518 by any suitable method including previously known methods. Within block 520, DDD biventricular pacing is enabled within the implantable device using the VVD provided via VV optimization and using AVD delays determined from the EMOTE values, as already described. It is noted that the order of steps 516 and 518 may be interchanged.

In view of the foregoing, it should be understood that using EMOTE-1 tends to promote LV hemodynamics to a greater extent than EMOTE-2, since sensing for EMOTE-1 is at the LA while sensing for EMOTE-2 is at the RA. Sensing more closely to the structure that actually fills the LV will intuitively yield a more accurate estimate of the optimal time to pace the LV. Again, it is noted that the timing cycles are based on atrial sense/pace to LV pace. The VV offset is used to determine when to deliver the RV pulse with respect to LV pacing.

Exemplary EMOAT Techniques for Use without External Calibration

FIGS. 10-14 illustrate various examples where electromechanical offset times are determined without the need for an external calibration system, i.e. the techniques exploit various EMOAT values. In a first example (FIGS. 10-12), the EMOAT values are determined by a pacer/CRT that employs an RA sensing channel during biventricular pacing to sense LA electrical activation using, e.g., RA tip/ring electrodes, and so the pacer/CRT uses EMOAT-2 values. In a second example, (FIGS. 13-14), the EMOAT values are determined by a pacer/CRT that employs a P4 sensing channel during biventricular pacing to sense the LA electrical activation and so the pacer/CRT uses EMOAT-1 values.

Many of the steps of the EMOAT embodiments are similar to corresponding steps of the EMOTE techniques, discussed above, and hence only significant differences will be explained in any detail. Note also that the numeral and alpha suffixes for EMOAT values are the same as those for the EMOTE values, namely -1 for offset from LA and -2 for offset from RA, -#i for intrinsic, -#r for RA-paced, and -#l for LA-paced. The method for determining actual times (EMOAT) as opposed to estimates (EMOTE) exploits a device-based sensor. For example, either a cardiogenic impedance signal based on the P4 electrode can be obtained for noting biatrial volumes or mitral annular motion time, or an accelerometer/heart sound sensor can be used to detect S1 early onset or mitral valve closure, for determining the actual "optimal" time for LV pacing based on LA active filling of the LV. As will be explained, in the case of EMOAT, the P4 sensed electrical signal triggers the beginning of a search window for impedance or sound-based determination of the actual mechanical activation time. It should be noted that there may be beat-to-beat differences in the time delay from the electrical and mechanical signals; therefore, EMOAT is preferred to EMOTE since EMOAT utilizes the beat-wise true optimized LV pace timing whereas EMOTE utilizes an estimate of the optimized LV pace timing based on the one-time calibration procedure. EMOAT can further cause the time between electrical sensed or event in the atria and LV pacing pulse to vary on a beat-by-beat basis, due to beatwise differences in electromechanical activation time (affected by heart rate, instantaneous neurohormonal state, etc.)

Figure 10:
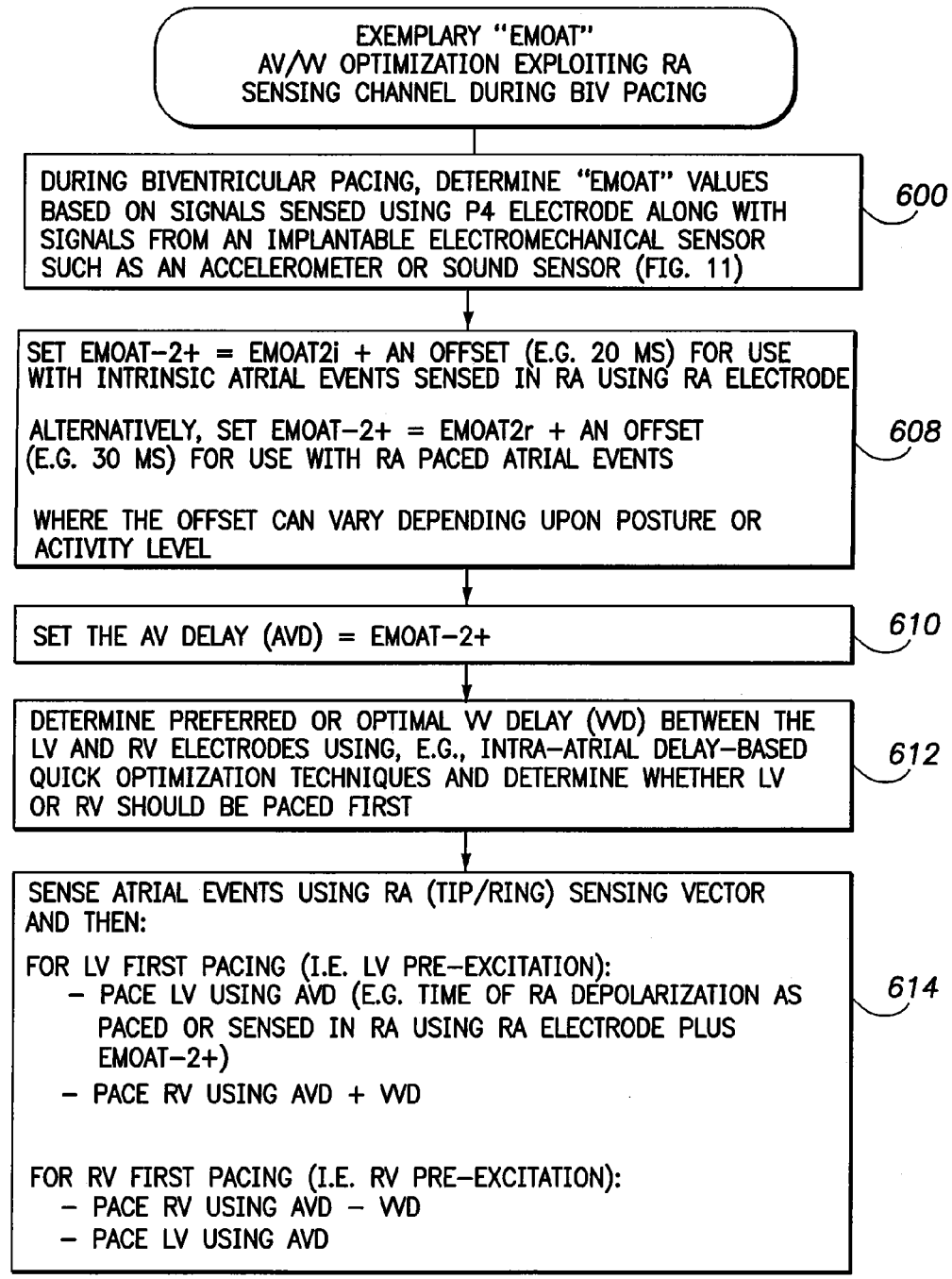
FIG. 10 is a flowchart illustrating a first exemplary EMOAT implementation of the method of FIG. 3 wherein an implantable sensor is employed to detect LA cardiomechanical delays for use in setting AV values for use with atrial events detected via an RA sensing channel of the device.
Figure 11:
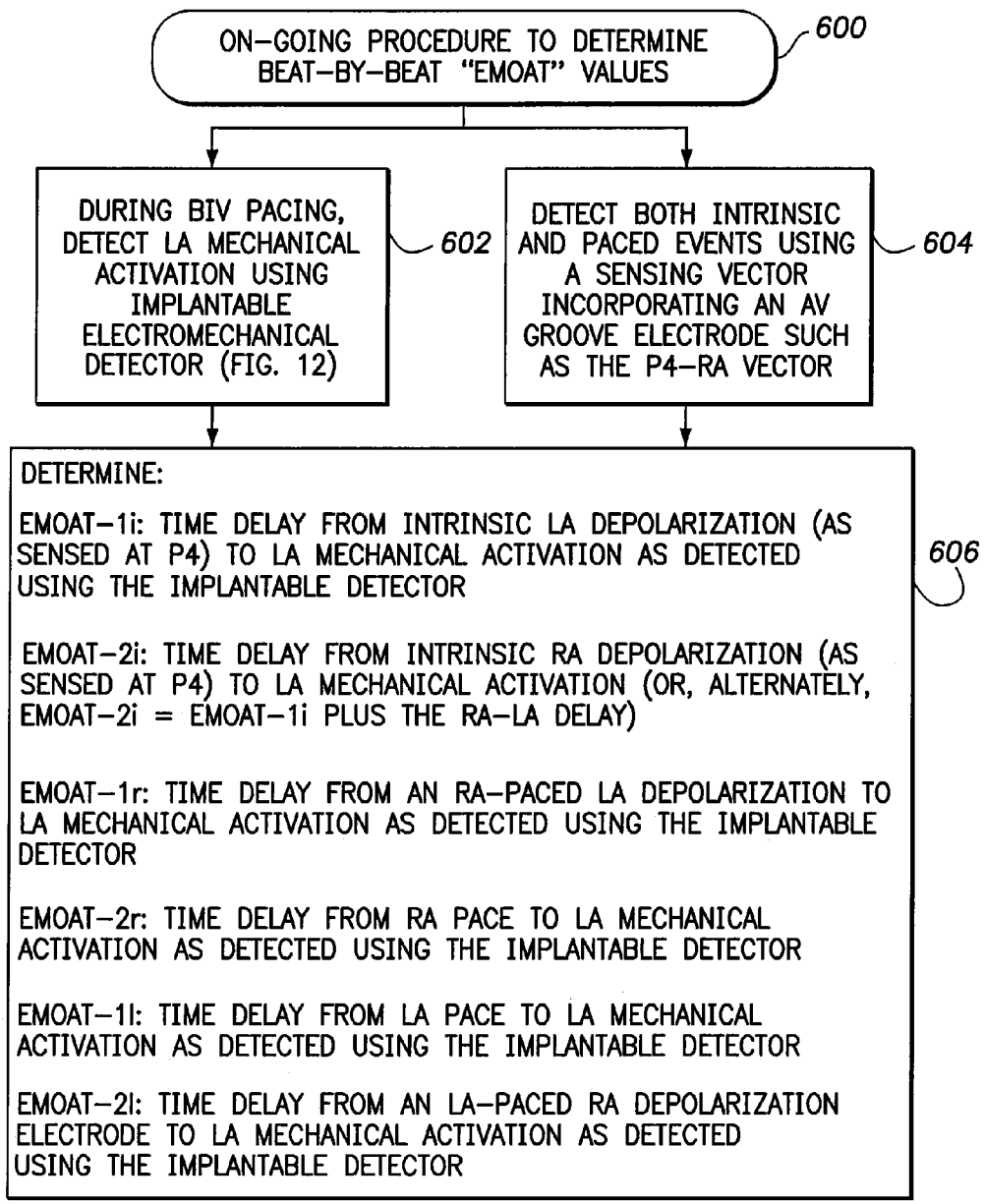
FIG. 11 is a flowchart illustrating exemplary techniques for determining EMOAT values for use with the technique of FIG. 10.

Beginning at step 600 of FIG. 10, during biventricular pacing, the implanted device determines EMOAT values based on signals sensed by the pacer/CRT using the P4 electrode along with inputs from an internal cardiomechanical detector, such as an accelerometer, heart sound detector, or cardiogenic impedance-based detection system. At step 602 of FIG. 11, the pacer/CRT system detects LA cardiomechanical activation using an implantable detection system (discussed below in FIG. 12.) Concurrently, at step 604, the pacer/CRT detects various intrinsic and paced atrial events using a P4 sensing vector. That is, at step 604, the time of LA electrical activation is detected. At step 606 of FIG. 11, the pacer/CRT determines:

EMOAT-1i: the time delay from an intrinsic LA depolarization (as sensed using P4) to LA cardiomechanical activation as detected using the implantable detector;

EMOAT-2i: the time delay from an intrinsic RA depolarization (as sensed using P4) to LA cardiomechanical activation (or, alternately, EMOAT-2i=EMOAT-1i+ the RA-LA delay, as detected by the pacer/CRT);

EMOAT-1r: the time delay from an RA-paced LA depolarization to LA cardiomechanical activation as detected using the implantable detector;

EMOAT-2r: the time delay from RA pace to LA cardiomechanical activation as detected using the implantable detector (where "RA pace" refers to the time at which a pacing pulse is delivered to the RA);

EMOAT-1l: the time delay from LA pace to LA cardiomechanical activation as detected using the implantable detector;

EMOAT-2l: the time delay from an LA-paced RA depolarization to LA cardiomechanical activation as detected using the implantable detector.

Returning to FIG. 10, at step 608, the pacer/CRT uses the EMOAT-2 value to set EMOAT-2+ values. More specifically, the pacer/CRT sets:

EMOAT-2+=EMOAT2i+an offset (e.g. 20 ms) for use with intrinsic atrial events sensed in RA via RA electrode; and EMOAT-2+=EMOAT2r+an offset (e.g. 30 ms) for use with paced atrial event where the offset is again selected so as to achieve maximum LV output. As discussed above, the offset can vary depending upon the heart rate, patient posture, activity level, or other factors.

At step 610, the pacer/CRT sets AVD to EMOAT-2+, where the value of EMOAT-2+ depends on whether the atrial event is paced or sensed. (Alternatively, the EMOAT-2+ value for use with sensed (i.e. intrinsic) events may be denoted "EMOAT-2i+" and the EMOAT-2+ value for use with paced events may be denoted "EMOAT-2r+".)

At step 612, the pacer/CRT determines the preferred or optimal VVD any suitable techniques and determines whether the LV or RV should be paced first. At step 614, during DDD pacing, the device senses atrial events, and/or paces the RA, using an RA sensing vector and then:

for LV first pacing (LV pre-excitation):
pace LV using AVD (e.g. the device adds AVD to the time of RA depolarization as sensed or paced using the RA lead)
pace RV using AVD+VVD
for RV first pacing (RV pre-excitation):
pace RV using AVD−VVD
pace LV using AVD.

Note that, since the EMOAT values are determined on a beat-by-beat basis by the pacer/CRT, the pacer/CRT does not periodically adjust the values based on changes in inter-atrial (RA-LA) conduction delay as with the EMOTE embodiments discussed above.

Figure 12:
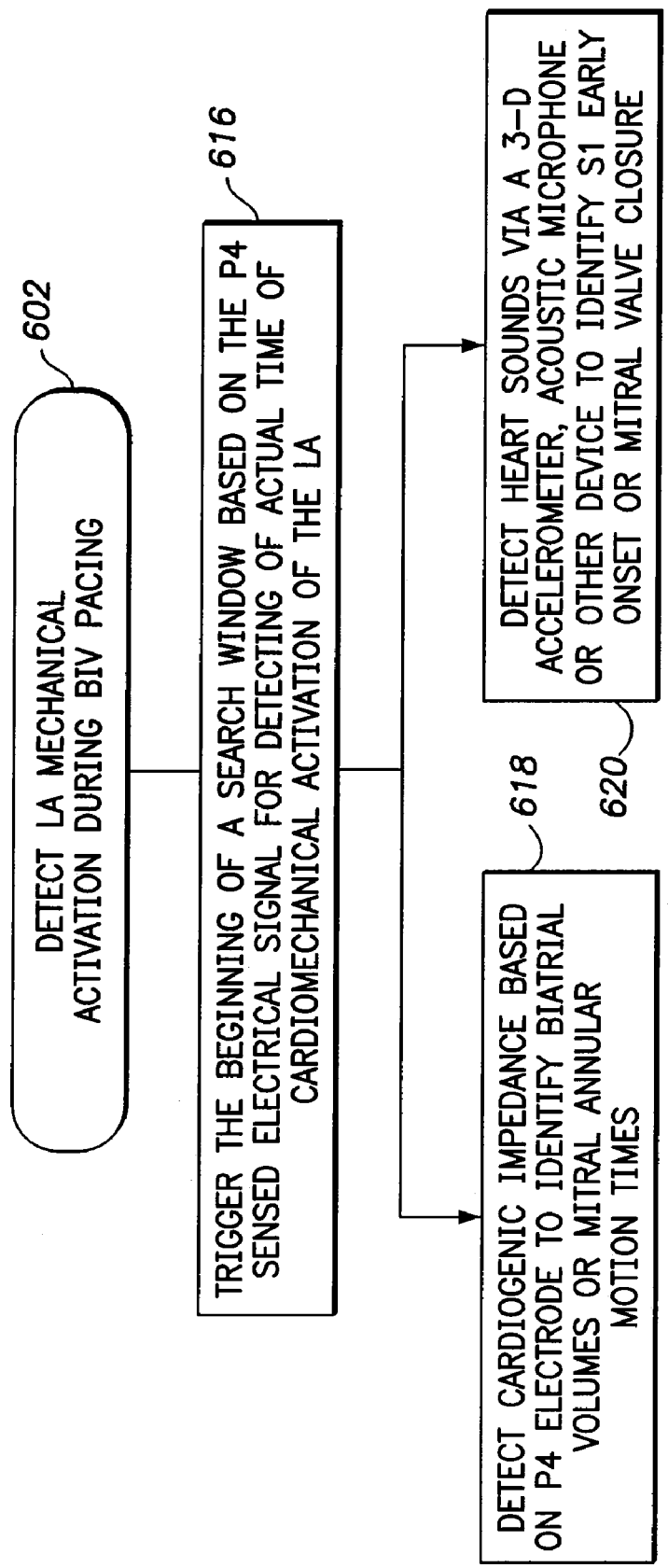
FIG. 12 is a flowchart illustrating exemplary techniques for detecting LA cardiomechanical activation using an implantable sensor for use with the technique of FIG. 11.

Turning now to FIG. 12, techniques for detecting LA cardiomechanical activation using an implantable detector will now be described further. Any of a variety of techniques may be exploited, alone or in combination, to detect the cardiomechanical activation. The two techniques described herein exploit cardiogenic impedance and heart sounds but other suitable techniques may be employed.

Briefly, at step 616, the device triggers the beginning of a search window based on the P4 sensed electrical signal for use with either the impedance-based or sound-based detection of the actual time of LA cardiomechanical contraction. Then, at step 618, cardiogenic impedance is detected based on P4 electrode (i.e. using a P4 impedance vector) to identify biatrial volumes or mitral annular motion times. Cardiogenic impedance is discussed, for example, in: U.S. patent application Ser. No. 11/558,194, by Panescu et al., entitled "Closed-Loop Adaptive Adjustment of Pacing Therapy based on Cardiogenic Impedance Signals Detected by an Implantable Medical Device". Additionally, or alternatively, at step 620, the device detects heart sounds via an accelerometer or other suitable device to identify S1 early onset or mitral valve closure. Techniques for detecting heart sounds are discussed in U.S. Pat. No. 6,477,406 to Turcott, entitled "Extravascular Hemodynamic Acoustic Sensor."

Figure 13:
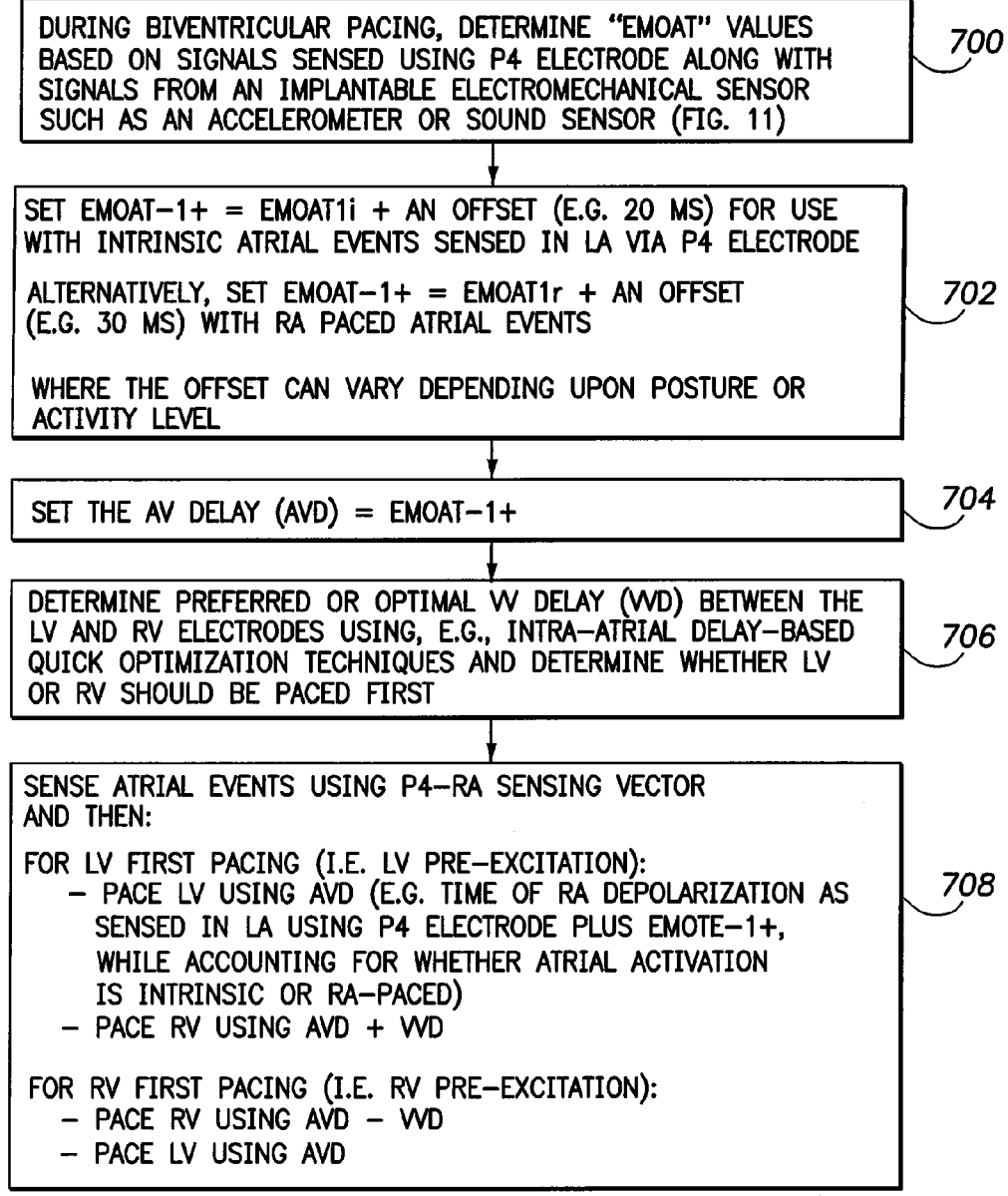
FIG. 13 is a flowchart illustrating a second exemplary EMOAT implementation of the method of FIG. 3 wherein an implantable sensor is employed to detect LA cardiomechanical events for use in setting AV values for use with atrial events detected via the P4 electrode sensing channel.
Figure 14:
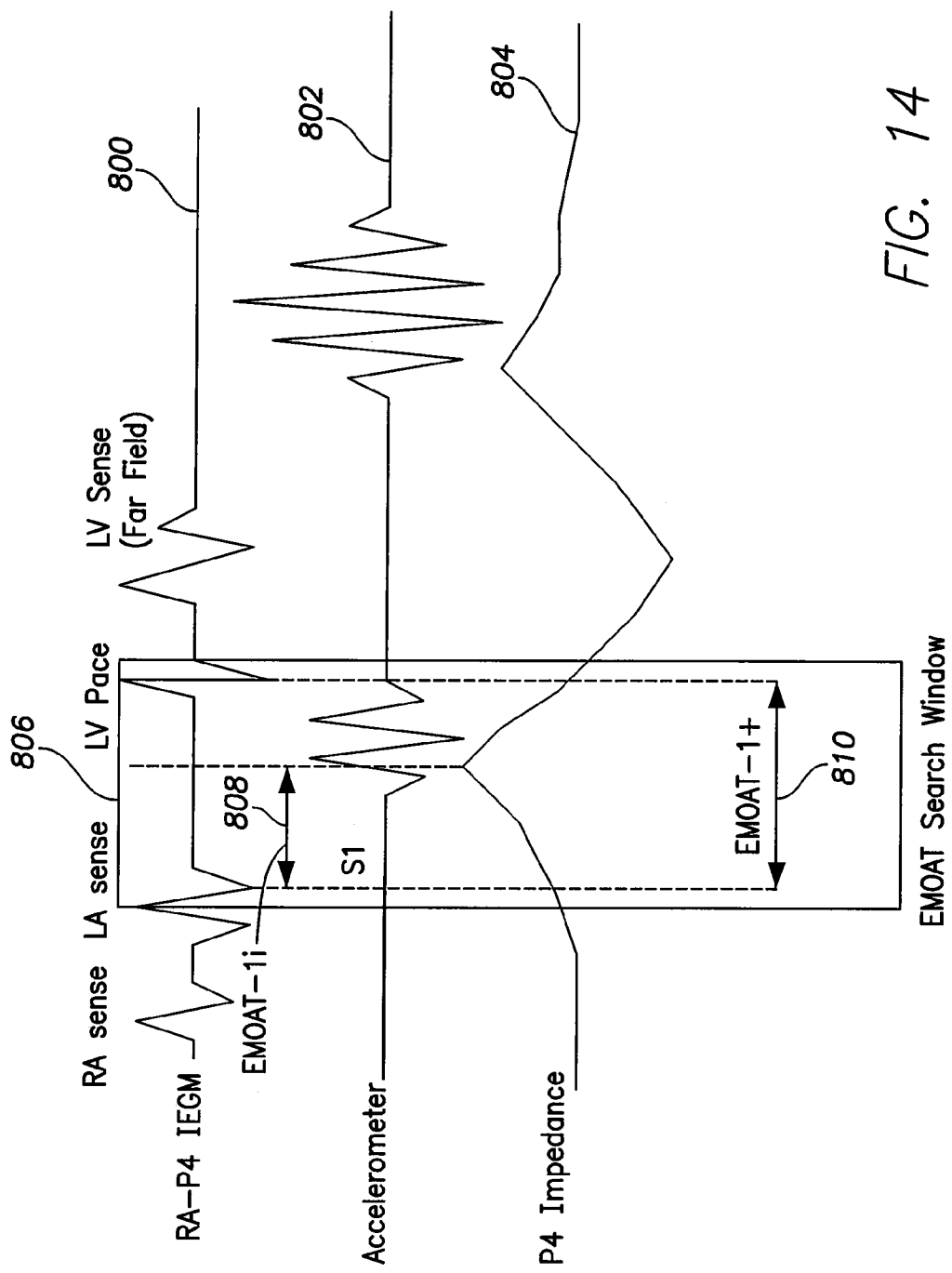
FIG. 14 includes timing diagrams illustrating exemplary EMOAT values exploited by the technique of FIG. 13.

Turning now to FIGS. 13 and 14, the second EMOAT example will now be described (which is employed with pacer/CRTs programmed to use a P4 sense channel during CRT to sense LA electrical events.) Again, many of the steps are the same or similar to that of the preceding embodiment and hence will not be described again in detail. Briefly, beginning at step 700 of FIG. 13, the pacer/CRT determines the aforementioned EMOAT values using the techniques of FIGS. 11 and 12, already described. At step 702 of FIG. 13, the pacer/CRT uses the EMOAT-1 values to set EMOAT-1+ values. More specifically, the pacer/CRT sets:

EMOAT-1+=EMOAT1i+an offset (e.g. 20 ms) for use with intrinsic atrial events sensed in RA via the P4 electrode; and EMOAT-1+=EMOAT1r+an offset (e.g. 30 ms) for use with paced atrial events.

where the offset can again vary depending upon the current patient posture and current activity level or other factors. As noted, this offset can differ from the other offset values described herein.

At step 704, the pacer/CRT then sets AVD to EMOAT-1+. At step 706, the pacer/CRT then determines VVD using suitable optimization techniques such as QuickOpt™ and determines whether LV or RV should be paced first. At step 708, during DDD pacing, the pacer/CRT senses intrinsic or RA-paced atrial events using a P4 sensing vector such as P4-RAring and then:

for LV first pacing (LV pre-excitation):
pace LV using AVD (e.g. the device adds AVD to the time of LA depolarization as sensed using the P4 sensing channel while accounting for whether atrial activation is intrinsic or RA-paced)
pace RV using AVD+VVD
for RV first pacing (RV pre-excitation):
pace RV using AVD−VVD
pace LV using AVD.

The P4 sensing vector that is used is preferably the P4-RAring vector because of a closer match in size between the P4 (ring) and RA ring electrodes. However, the RA tip (in either a helix or passive fixation configuration) could instead be used. The latter may simply change the relative size or sharpness of the RA versus LA components of the IEGM signal.

FIG. 14 provides timing diagrams illustrating features of the EMOAT embodiments. Timing diagram 800 shows the RA-P4 IEGM, including various paced and sensed events. Timing diagram 802 shows the output from an accelerometer positioned to detect LA mechanical activation via the S1 heart sound. Timing diagram 804 shows the output from a cardiogenic impedance detector equipped to detect cardiogenic impedance via the P4 electrode. As can be seen, both the accelerometer signal and the impedance signal include deflections representative of LA mechanical contraction. The aforementioned search window, which begins upon the peak of the LA sense waveform, is shown by way of shaded area 806. The EMOTE-1i time interval from the end of the LA sense to the time of LA mechanical activation is shown by way of interval 808. The longer EMOTE-1+ interval (which corresponds to AVD and is equal to EMOTE-1i plus an offset) is shown by way of interval 810. Note that, in this particular example, the time of LA mechanical activation is set to the peak of the P4 impedance signal, which is approximately aligned with the onset or peak in the first S1 heart sound (as detected via the accelerometer signal). It is believed—based on the relationship of the accelerometer and impedance signals—that the two signals are typically aligned, at least approximately though not necessarily precisely. In other examples, other points within the heart sound and/or cardiogenic impedance signal can be used to represent the point of LA mechanical activation.

What have been described are various techniques for optimizing AV/VV delays for use with biventricular pacing. It should be understood that these optimized values are not necessarily truly optimal in any particular quantifiable sense. As can be appreciated, what constitutes a truly "optimal" value depends on the criteria used for judging the resulting performance, which can be subjective in the minds of some clinicians. Accordingly, the pacing delay values provided herein are at least preferred delay values. Clinicians may choose to adjust or alter the selection via device programming for particular patients, at their discretion. Note also that, in the examples described herein, the multi-pole ventricular lead is an LV lead, but it should be understood that aspects of the invention are applicable to multi-pole RV leads. Indeed, at least some of the techniques described herein are generally applicable to implementations wherein both the LV and RV have multi-pole leads. At least some of the techniques might be applicable to multi-pole atrial leads, implanted on or in either the RA or the LA/CS.

Still further, where appropriate, the techniques described herein might be employed in combination with other AV/VV optimization techniques to, for example, provide for corroboration. The following patents and patent applications set forth various systems and methods for determining and/or adjusting AV/VV pacing delays so as to help maintain the pacing delays at preferred or optimal values: U.S. Pat. No. 7,590,446 (cited above); U.S. Published Patent Application 2009/0299423 (cited above); U.S. patent application Ser. No. 11/952,743 (cited above); U.S. Published Patent Application No. 2010/0145405 (cited above); U.S. Published Patent Application No. 2011/0022110; U.S. Published Patent Application No. 2011/0022112; and U.S. patent application Ser. No. 12/604,280, filed Oct. 22, 2009 of Min et al., entitled "Systems and Methods for Determining Optimal Electrode Pairs for use in Biventricular Pacing using Multi-Pole Ventricular Leads".

Insofar as AV optimization is concerned, see also U.S. Patent Application 2007/0093872 of Chirife et al. "System and Method of AV Interval Selection in an Implantable Medical Device."

Moreover, it should be appreciated that the foregoing descriptions provide, among other features, for the following: (a) proximal electrode sensing for left atrial electrical activation during CRT to aid in timing for optimal LV filling; (c) a calibration procedure to determine Electro-Mechanical Offset Time Estimate from RA or LA electrical sense to LA mechanical event such as completion of LA contraction or onset of mitral valve closure and further programming of electromechanical offset time estimate as delay between atrial electrical event (paced or sensed) and LV stimulation pulse; and (c) the utilization of device-based sensors for beat-to-beat LA mechanical event detection (Electro-Mechanical Offset Actual Time), specifically P4 electrode impedance peak indicating full emptying of atria or specifically first onset of passive mitral closure heart sound, and further programming actual time as a dynamic delay between atrial event and LV stimulation pulse Although primarily described with respect to examples having a CRT with defibrillation capability (i.e. a CRT-D), other implantable medical devices may be equipped to exploit the techniques described herein such as standalone CRT devices or CRT-P devices (i.e. a CRT device not equipped to deliver defibrillation shocks.) For the sake of completeness, an exemplary pacer/ICD/CRT will now be described, which includes components for performing the functions and steps already described, as well as components for controlling CRT.

Exemplary Pacer/CRT

Figure 15:
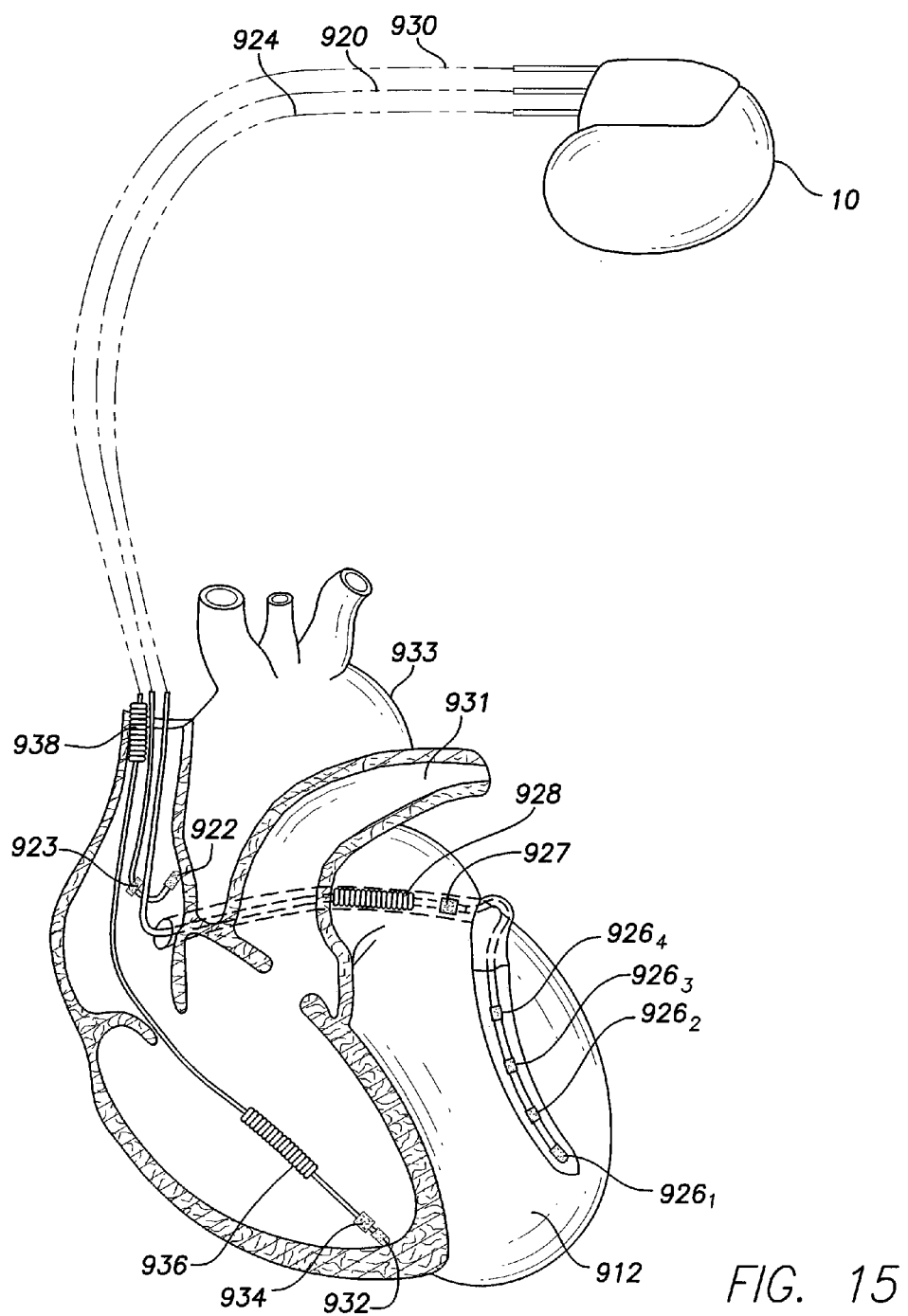
FIG. 15 is a simplified, partly cutaway view, illustrating the device of FIGS. 1 and 2 along with at set of leads implanted into the heart of the patient.
Figure 16:
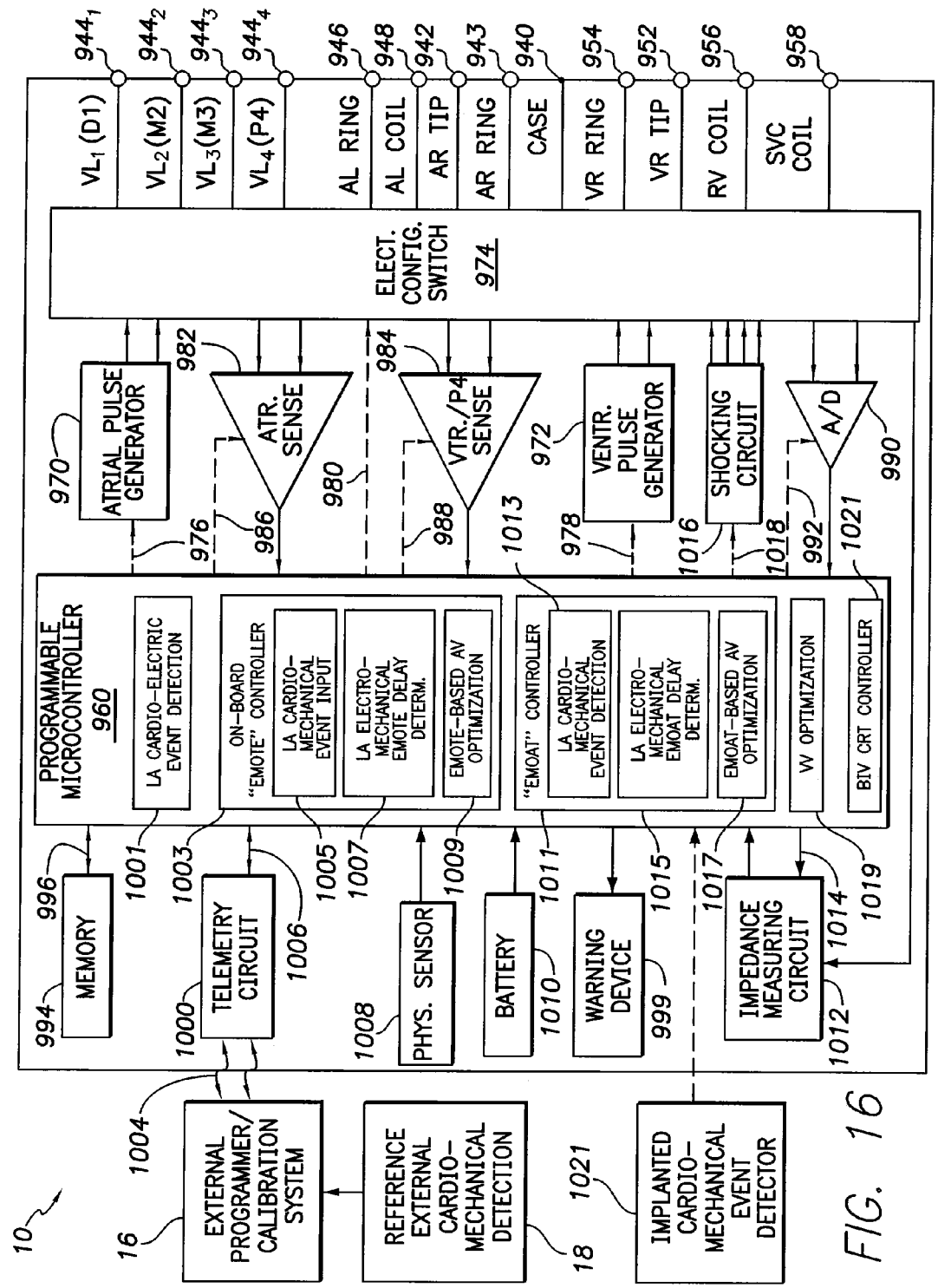
FIG. 16 is a functional block diagram of the pacer/CRT of FIG. 15, illustrating basic circuit elements that provide cardioversion, defibrillation and/or pacing stimulation in the heart an particularly illustrating on-board optimization components for controlling the optimization techniques of FIGS. 3-14.

With reference to FIGS. 15 and 16, a description of an exemplary pacer/CRT will now be provided. FIG. 15 provides a simplified block diagram of the pacer/CRT, which is a dual-chamber stimulation device capable of treating both fast and slow arrhythmias with stimulation therapy, including cardioversion, defibrillation, and pacing stimulation, and also capable of setting and using AV/VV pacing delays, as discussed above. To provide other atrial chamber pacing stimulation and sensing, pacer/CRT 10 is shown in electrical communication with a heart 912 by way of a left atrial lead 920 having an atrial tip electrode 922 and an atrial ring electrode 923 implanted in the atrial appendage. Pacer/CRT 10 is also in electrical communication with the heart by way of a right ventricular lead 930 having, in this embodiment, a ventricular tip electrode 932, a right ventricular ring electrode 934, a right ventricular (RV) coil electrode 936, and a superior vena cava (SVC) coil electrode 938. Typically, the right ventricular lead 930 is transvenously inserted into the heart so as to place the RV coil electrode 936 in the right ventricular apex, and the SVC coil electrode 938 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/CRT 10 is coupled to a multi-pole LV lead 924 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 924 is designed to receive atrial and ventricular cardiac signals and to deliver left ventricular pacing therapy using a set of four left ventricular electrodes $926_1$ (D1), $926_2$ (M2), $926_3$ (M3), and $926_4$ (P4), (thereby providing a quad-pole lead), left atrial pacing therapy using at least a left atrial ring electrode 927, and shocking therapy using at least a left atrial coil electrode 928. The $926_1$ LV electrode may also be referred to as a "tip" or "distal" LV electrode. The $926_4$ LV electrode may also be referred to as a "proximal" LV electrode. In other examples, more or fewer LV electrodes are provided. Although only three leads are shown in FIG. 15, it should also be understood that additional leads (with one or more pacing, sensing and/or shocking electrodes) might be used and/or additional electrodes might be provided on the leads already shown, such as additional electrodes on the RV lead. Also, note that the P4 electrode $926_4$ is preferably located in or near the AV groove, as discussed and described above. The details of this configuration are not necessarily shown in this particular figure.

It is noted that, in practice, electrodes 926 are on the "left heart lead" and depending upon where the lead is implanted, in most patients, all four electrodes can be in LV but in a substantial minority of patients the P4 electrode is situated in the LA (specifically in AV groove). As noted above, the P4 electrode is the electrode on which LA activation is sensed (which can also be present even if the electrode is primarily on the LV instead of LA). On present commercially-available hardware, there is often no separate electrode 927. That is, the P4 electrode $926_4$ and the "left atrial ring electrode" 927 are one and the same. Hence, it should be understood that the "left atrial ring electrode" could instead be used as the P4 electrode, assuming it is suitably positioned in or near the AV groove. Both electrodes are shown for the sake of completeness and generality.

A simplified block diagram of internal components of pacer/CRT 10 is shown in FIG. 16. While a particular pacer/CRT is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 940 for pacer/CRT 10, shown schematically in FIG. 16, is often referred to as the "can", "case" or "case electrode" and may be programmably selected to act as the return electrode for all "unipolar" modes. The housing 940 may further be used as a return electrode alone or in combination with one or more of the coil electrodes, 928, 936 and 938, for shocking purposes. The housing 940 further includes a connector (not shown) having a plurality of terminals, 942, 943, 944$_1$-944$_4$, 946, 948, 952, 954, 956 and 958 (shown schematically and, for convenience, the names of the electrodes to which they are connected are shown next to the terminals). As such, to achieve right atrial sensing and pacing, the connector includes at least a right atrial tip terminal (A$_R$ TIP) 942 adapted for connection to the atrial tip electrode 922 and a right atrial ring (A$_R$ RING) electrode 943 adapted for connection to right atrial ring electrode 923. To achieve left chamber sensing, pacing and shocking, the connector includes a left ventricular tip terminal (VL$_1$ TIP) 944$_1$ and additional LV electrode terminals 944$_2$-944$_4$ for the other LV electrodes of the LV lead.

The connector also includes a left atrial ring terminal (A$_L$ RING) 946 and a left atrial shocking terminal (A$_L$ COIL) 948, which are adapted for connection to the left atrial ring electrode 927 and the left atrial coil electrode 928, respectively. To support right chamber sensing, pacing and shocking, the connector further includes a right ventricular tip terminal (V$_R$ TIP) 952, a right ventricular ring terminal (V$_R$ RING) 954, a right ventricular shocking terminal (V$_R$ COIL) 956, and an SVC shocking terminal (SVC COIL) 958, which are adapted for connection to the right ventricular tip electrode 932, right ventricular ring electrode 934, the V$_R$ coil electrode 936, and the SVC coil electrode 938, respectively.

At the core of pacer/CRT 10 is a programmable microcontroller 960, which controls the various modes of stimulation therapy. As is well known in the art, the microcontroller 960 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 960 includes the ability to process or monitor input signals (data) as controlled by a program code stored in a designated block of memory. The details of the design and operation of the microcontroller 960 are not critical to the invention. Rather, any suitable microcontroller 960 may be used that carries out the functions described herein. The use of microprocessor-based control circuits for performing timing and data analysis functions are well known in the art.

As shown in FIG. 16, an atrial pulse generator 970 and a ventricular pulse generator 972 generate pacing stimulation pulses for delivery by the right atrial lead 920, the right ventricular lead 930, and/or the LV lead 924 via an electrode configuration switch 974. It is understood that in order to provide stimulation therapy in each of the four chambers of the heart, the atrial and ventricular pulse generators, 970 and 972, may include dedicated, independent pulse generators, multiplexed pulse generators or shared pulse generators. The pulse generators, 970 and 972, are controlled by the microcontroller 960 via appropriate control signals, 976 and 978, respectively, to trigger or inhibit the stimulation pulses.

The microcontroller 960 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 974 includes a plurality of switches for connecting the desired electrodes to the appropriate I/O circuits, thereby providing complete electrode programmability. Accordingly, the switch 974, in response to a control signal 980 from the microcontroller 960, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 982 and ventricular sensing circuits 984 may also be selectively coupled to the right atrial lead 920, LV lead 924, and the right ventricular lead 930, through the switch 974 for detecting the presence of cardiac activity in each of the four chambers of the heart. The ventricular sense circuit preferably accommodates at least one P4 sensing channel. Accordingly, the atrial (ATR. SENSE) and ventricular (VTR. SENSE) sensing circuits, 982 and 984, may include dedicated sense amplifiers, multiplexed amplifiers or shared amplifiers. The switch 974 determines the "sensing polarity" of the cardiac signal by selectively closing the appropriate switches, as is also known in the art. In this way, the clinician may program the sensing polarity independent of the stimulation polarity. Each sensing circuit, 982 and 984, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/CRT 10 to deal effectively with the difficult problem of sensing the low amplitude signal characteristics of atrial or ventricular fibrillation. The outputs of the atrial and ventricular sensing circuits, 982 and 984, are connected to the microcontroller 960 which, in turn, are able to trigger or inhibit the atrial and ventricular pulse generators, 970 and 972, respectively, in a demand fashion in response to the absence or presence of cardiac activity in the appropriate chambers of the heart.

For arrhythmia detection, pacer/CRT 10 utilizes the atrial and ventricular sensing circuits, 982 and 984, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 960 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 990. The data acquisition system 990 is configured to acquire intracardiac electrogram signals, convert the raw analog data into a digital signal, and store the digital signals for later processing and/or telemetric transmission to an external device 1002. The data acquisition system 990 is coupled to the right atrial lead 920, the LV lead 924, and the right ventricular lead 930 through the switch 974 to sample cardiac signals across any pair of desired electrodes. The microcontroller 960 is further coupled to a memory 994 by a suitable data/address bus 996, wherein the programmable operating parameters used by the microcontroller 960 are stored and modified, as required, in order to customize the operation of pacer/CRT 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/CRT 10 may be non-invasively programmed into the memory 994 through a telemetry circuit 1000 in telemetric communication with the external device 1002, such as a programmer, transtelephonic transceiver or a diagnostic system analyzer. The telemetry circuit 1000 is activated by the microcontroller by a control signal 1006. The telemetry circuit 1000 advantageously allows intracardiac electrograms and status information relating to the operation of pacer/CRT 10 (as contained in the microcontroller 960 or memory 994) to be sent to the external device 1002 through an established communication link 1004. Pacer/CRT 10 further includes an accelerometer or other physiologic sensor 1008, commonly referred to as a "rate-responsive" sensor because it is typically used to adjust pacing stimulation rate according to the exercise state of the patient. However, the physiological sensor 1008 may further be used to detect changes in cardiac output, changes in the physiological condition of the heart, or diurnal changes in activity (e.g., detecting sleep and wake states) and to detect arousal from sleep. Accordingly, the microcontroller 960 responds by adjusting the various pacing parameters (such as rate, AV delay, VV delay, etc.) at which the atrial and ventricular pulse generators, 970 and 972, generate stimulation pulses. While shown as being included within pacer/CRT 10, it is to be understood that the physiologic sensor 1008 may also be external to pacer/CRT 10, yet still be implanted within or carried by the patient. A common type of rate responsive sensor is an activity sensor incorporating an accelerometer or a piezoelectric crystal, which is mounted within the housing 940 of pacer/CRT 10. Other types of physiologic sensors are also known, for example, sensors that sense the oxygen content of blood, respiration rate and/or minute ventilation, pH of blood, ventricular gradient, etc.

The pacer/CRT additionally includes a battery 1010, which provides operating power to all of the circuits shown in FIG. 16. The battery 1010 may vary depending on the capabilities of pacer/CRT 10. If the system only provides low voltage therapy, a lithium iodine or lithium copper fluoride cell typically may be utilized. For pacer/CRT 10, which employs shocking therapy, the battery 1010 should be capable of operating at low current drains for long periods, and then be capable of providing high-current pulses (for capacitor charging) when the patient requires a shock pulse. The battery 1010 should also have a predictable discharge characteristic so that elective replacement time can be detected. Accordingly, appropriate batteries are employed.

As further shown in FIG. 16, pacer/CRT 10 is shown as having an impedance measuring circuit 1012, which is enabled by the microcontroller 960 via a control signal 1014. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, and detecting cardiogenic impedance, etc. The impedance measuring circuit 1012 is advantageously coupled to the switch 1074 so that any desired electrode may be used, including the P4 electrode.

In the case where pacer/CRT 10 is intended to operate as an ICD device, it detects the occurrence of an arrhythmia, and automatically applies an appropriate electrical shock therapy to the heart aimed at terminating the detected arrhythmia. To this end, the microcontroller 960 further controls a shocking circuit 1016 by way of a control signal 1018. The shocking circuit 1016 generates shocking pulses of low (up to 0.5 joules), moderate (0.5-10 joules) or high energy (11 to 40 joules or more), as controlled by the microcontroller 960. Such shocking pulses are applied to the heart of the patient through at least two shocking electrodes, and as shown in this embodiment, selected from the left atrial coil electrode 928, the RV coil electrode 936, and/or the SVC coil electrode 938. The housing 940 may act as an active electrode in combination with the RV electrode 936, or as part of a split electrical vector using the SVC coil electrode 938 or the left atrial coil electrode 928 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 960 is capable of controlling synchronous or asynchronous delivery of shocking pulses.

An internal warning device 999 may be provided for generating perceptible warning signals to the patient via vibration, voltage or other methods.

Insofar as EMOTE/EMOAT processing is concerned, the microcontroller includes an LA cardioelectric event detection system 1001 operative to sense LA electrical depolarization events using the proximal electrode (P4) of the LV lead or other suitable electrodes in or near the AV groove. In this example, an on-board EMOTE controller 1003 is provided that determines the above-described EMOTE values using data received from an external reference calibration system. (In other examples, the determination of the EMOTE values is instead performed by the external calibration system and then the values are programmed into the implanted device.) Within the on-board EMOTE implementation, the EMOTE controller includes an LA cardiomechanical event input system 1005 operative to input LA cardiomechanical event data generated during calibration by the external cardiomechanical detection system 18 (echocardiography, sonocardiography, etc.) and received via the telemetry circuit. Additionally, or alternatively, the on-board system may contain circuitry to detect LA cardiomechanical events on its own. For example, a suitable device-based impedance or accelerometer can be used during the calibration procedure to determine the electromechanical offset time estimates. This differs from EMOAT in that in the examples described herein EMOAT uses on-board sensors for ongoing beat-to-beat changes; whereas EMOTE can use external or on-board sensors for one-time (and/or occasionally repeated) calibrations. The on-board EMOTE controller also includes an LA electromechanical EMOTE delay determination system 1007, which is operative to determine the aforementioned LA electromechanical EMOTE delays (EMOTE-1i, EMOTE-2i, etc.) between the LA electrical depolarization event and the LA mechanical event. An EMOTE-based AV optimization system determines preferred or optimal AV delay values based on the EMOTE values using techniques already described.

Additionally or alternatively, an EMOAT controller 1011 is provided that determines the various above-described EMOAT values using data received from an implantable electromechanical event detector 1021, which may include an accelerometer, acoustic heart sound detector or other suitable device. Depending upon the implementation, the detector 1021 might be mounted to one of the leads and hence is shown in FIG. 16 as being external to the pacer/CRT itself. Additional connection terminals (not shown in the figure) can be provided for receiving signals from detector 1021. The EMOAT controller includes an LA cardiomechanical event detection system 1013 operative to process LA cardiomechanical event data received from detector 1021 to detect LA mechanical activation. The EMOAT controller also includes an LA electromechanical EMOAT delay determination system 1015, which is operative to determine the aforementioned LA electromechanical EMOAT delays (EMOAT-1i, EMOAT-2i, etc.) between the LA electrical depolarization event and the LA mechanical event. An EMOAT-based AV optimization system determines preferred or optimal AV delay values based on the EMOAT delays using techniques already described.

A VV optimization system 1019 controls the determination of VV delays, and the determination of the order with which the RV and LV are to be stimulated, using techniques already discussed. A biventricular CRT controller 1021 is operative to controlling pacing using the AV/VV pacing delays. Diagnostic data can be stored within memory 994. Warning signals, if warranted, may be generated via warning device 999. Warning signals may be appropriate if the on-board optimization components are unable to properly optimize the AV/VV delays due, for example, to poor signal quality from the P4 electrode sensing channel.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, a detailed description of an exemplary device programmer/calibration system will now be provided.

Exemplary External Programmer

Figure 17:
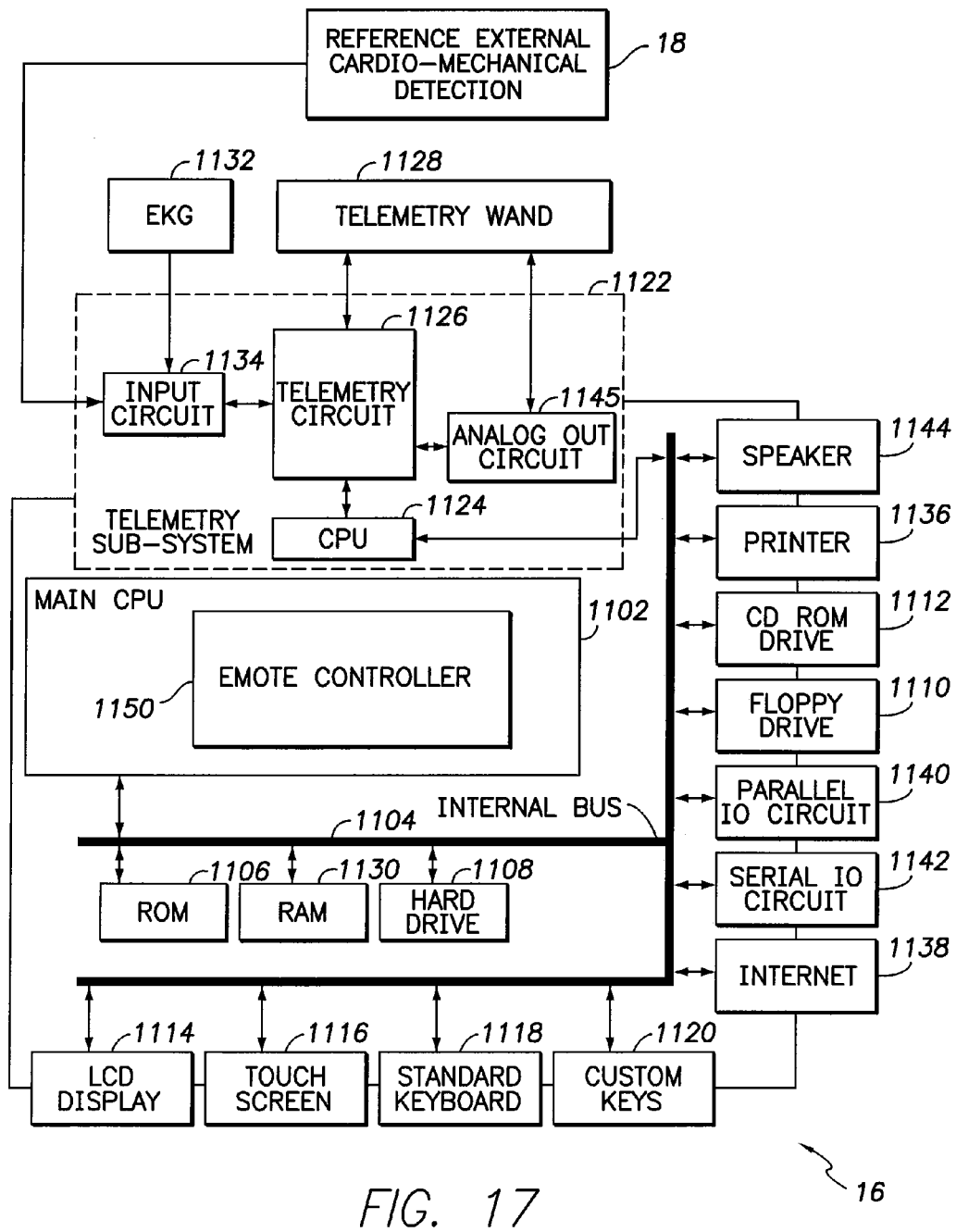
FIG. 17 is a functional block diagram illustrating components of the external programmer of FIG. 1, particularly illustrating programmer-based systems for controlling the optimization techniques of FIGS. 3-14.

FIG. 17 illustrates pertinent components of an external programmer 16 for use in programming the pacer/CRT of FIGS. 15 and 16 and for performing the above-described optimization techniques. For the sake of completeness, other device programming functions are also described herein. Generally, the programmer permits a physician, clinician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 16 may also be capable of processing and analyzing data received from the implanted device and from the EKG leads to, for example, render preliminary diagnosis as to medical conditions of the patient or to the operations of the implanted device.

Now, considering the components of programmer 16, operations of the programmer are controlled by a CPU 1102, which may be a generally programmable microprocessor or microcontroller or may be a dedicated processing device such as an application specific integrated circuit (ASIC) or the like. Software instructions to be performed by the CPU are accessed via an internal bus 1104 from a read only memory (ROM) 1106 and random access memory 1130. Additional software may be accessed from a hard drive 1108, floppy drive 1110, and CD ROM drive 1112, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 1114 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 1116 overlaid on the LCD display or through a standard keyboard 1118 supplemented by additional custom keys 1120, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 16 to retrieve data stored within any implanted devices and to also retrieve EKG data from EKG leads, if any, coupled to the patient. To this end, CPU 1102 transmits appropriate signals to a telemetry subsystem 1122, which provides components for directly interfacing with the implanted devices, and the EKG leads. Telemetry subsystem 1122 includes its own separate CPU 1124 for coordinating the operations of the telemetry subsystem. Main CPU 1102 of programmer communicates with telemetry subsystem CPU 1124 via internal bus 1104. Telemetry subsystem additionally includes a telemetry circuit 1126 connected to telemetry wand 1128, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an input circuit 1134 for receiving surface EKG signals from a surface EKG system 1132. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/CRT also includes the data stored within the recalibration database of the pacer/CRT (assuming the pacer/CRT is equipped to store that data.) Data retrieved from the implanted devices is stored by external programmer 16 either within a random access memory (RAM) 1130, hard drive 1108 or within a floppy diskette placed within floppy drive 1110. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 16, the implanted devices may be further controlled to transmit additional data in real time as it is detected by the implanted devices, such as additional IEGM data, lead impedance data, and the like. Additionally, or in the alternative, telemetry subsystem 1122 receives EKG signals from EKG leads 1132 via an EKG processing circuit 1134. As with data retrieved from the implanted device itself, signals received from the EKG leads are stored within one or more of the storage devices of the external programmer. Typically, EKG leads output analog electrical signals representative of the EKG. Accordingly, EKG circuit 1134 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 1102, the programming commands are converted to specific programmable parameters for transmission to the implanted devices via telemetry wand 1128 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 1136.

Programmer/monitor 16 also includes an internet connection 1138 to permit direct transmission of data to other programmers via the public switched telephone network (PSTN) or other interconnection line, such as a T1 line, fiber optic cable, Wi-Fi, cellular network, etc. Depending upon the implementation, the modem may be connected directly to internal bus 1104 may be connected to the internal bus via either a parallel port 1140 or a serial port 1142. Other peripheral devices may be connected to the external programmer via parallel port 1140 or a serial port 1142 as well. Although one of each is shown, a plurality of input output (IO) ports might be provided. A speaker 1144 is included for providing audible tones to the user, such as a warning beep in the event improper input is provided by the physician. Telemetry subsystem 1122 additionally includes an analog output circuit 1145 for controlling the transmission of analog output signals, such as IEGM signals output to an EKG machine or chart recorder.

Insofar as AV/VV optimization pacing is concerned, main CPU 1102 includes an EMOTE controller 1150 operative to control the generation of EMOTE values for programming the pacer/CRT. The EMOTE controller receives LA cardiomechanical event data from the reference detection system 18 (echocardiography, sonocardiography, etc.) via the input circuit or from device-based sensors. The EMOTE controller also receives LA cardioelectrical event data (from the P4 sensing vector) from the implanted device via the telemetry circuit. The EMOTE controller then determines the aforementioned LA electromechanical EMOTE delays (EMOTE-1i, EMOTE-2i, etc.) between the LA electrical depolarization event and the LA mechanical event and programs those delays into the pacer/CRT for use therein in determining AV delays and controlling CRT. Depending upon the implementation, the various components of the CPU may be implemented as separate software modules or the modules may be combined to permit a single module to perform multiple functions. In addition, although shown as being components of the CPU, some or all of these components may be implemented separately, using ASICs or the like.

With the programmer configured as shown, a clinician or other user operating the external programmer is capable of retrieving, processing and displaying a wide range of information received from the implanted device and to reprogram the implanted device if needed.

The descriptions provided herein with respect to FIG. 16 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable cardiac stimulation device equipped with a left ventricular (LV) lead having at least one proximal electrode implanted near an atrioventricular (AV) groove of the heart of the patient, the method comprising:
   sensing a left atrial (LA) cardioelectrical event using the proximal electrode of the LV lead;
   detecting a corresponding LA cardiomechanical event in response to the sensed cardioelectrical event utilizing at least one of echocardiography, sonocardiography and impedance cardiography, wherein the LA cardiomechanical event corresponds to one or more of: i) completion of an atrial kick, ii) closure of a mitral valve, and iii) onset, peak and/or completion of an A-wave of a mitral valve annulus;
   determining an LA electromechanical delay between the LA cardioelectrical event and the LA cardiomechanical event;
   determining pacing delays based on the LA electromechanical delay for use in
   delivering pacing using the lead; and
   controlling pacing using the pacing delays.

2. The method of claim 1 for use with an implantable cardiac stimulation device is additionally equipped with a right atrial (RA) lead having at least one electrode in the RA and wherein the method further comprises:
   sensing an RA cardioelectrical event using the electrode of the RA lead;
   detecting the corresponding LA cardiomechanical event in response to the sensed electrical event;

determining an RA-LA electromechanical delay between the RA cardioelectrical event and the LA cardiomechanical event;
determining pacing delays based on the RA-LA electromechanical delay for use in delivering pacing using the lead.

3. The method of claim 1 wherein the LA cardioelectrical event corresponds to electrical depolarization of the LA.

4. The method of claim 1 further comprising:
detecting intrinsic and paced cardiac events within the heart of the patient using a P4 electrode;
determining a set of Electro-Mechanical Offset Actual Time (EMOAT) values based on intrinsic and paced events and the LA cardiomechanical events;
wherein the first and second EMOATs are based in part on intrinsic and paced events, respectfully.

5. The method of claim 1 wherein the pacing delays include AV pacing delays for use with biventricular cardiac resynchronization therapy (CRT).

6. The method of claim 1 wherein determining the pacing delays based on the LA electromechanical delay is performed to set pacing delays to provide for delivery of an LV pacing pulse at a time of optimal left heart filling.

7. The method of claim 1 for use with an implantable device equipped for biventricular pacing wherein the LV lead is a multi-polar lead having a proximal electrode (P4) implanted near the AV groove and wherein sensing the LA cardioelectrical event using the proximal electrode (P4) is performed using a sensing vector coupled to the P4 electrode.

8. The method of claim 7 wherein the P4 sensing vector includes one or more of: a P4-case vector, a P4-RVcoil vector, a P4-RAring vector and a P4-non P4 LV electrode vector and a P4-any other electrode in the heart vector.

9. The method of claim 7 wherein the implantable device is equipped with an implantable cardiomechanical event detector and wherein the step of detecting an LA cardiomechanical event is performed using the implantable detector during on-going pacing.

10. The method of claim 1 wherein the steps of sensing the LA cardioelectrical event, detecting the LA cardiomechanical event, determining the LA electromechanical delay, and determining the pacing delays further comprise:
detecting intrinsic and paced cardiac events within the heart of the patient using a P4 electrode;
detecting corresponding LA cardiomechanical events using an implantable detector;
determining a set of Electro-Mechanical Offset Actual Time (EMOAT) values based on intrinsic and paced events and the LA cardiomechanical events;
determining interventricular (VV) pacing delay values (VVD);
determining an excitation order for biventricular pacing specifying LV first pacing or RV first pacing; and
setting AV pacing delay values (AVD) based on the EMOAT values, the VVD values and the biventricular pacing excitation order.

11. The method of claim 10 wherein detecting the LA cardiomechanical events using the implantable atrial mechanical event detector includes one or more of:
detecting cardiogenic impedance using on the P4 electrode to identify one or more of biatrial volumes or a mitral annular motion time; and
detecting heart sounds to identify one or more of an S1 early onset or a mitral valve closure.

12. The method of claim 11 wherein detecting the LA cardiomechanical events using the implantable atrial mechanical event detector is performed within a detection window triggered by based on the P4-sensed cardioelectrical event.

13. The method of claim 10 wherein determining the set of EMOAT values includes:
determining an EMOAT-1i value representing a time delay from an intrinsic LA depolarization as sensed at P4 to the LA cardiomechanical activation as detected using the implantable detector;
determining an EMOAT-2i value representing a time delay from an intrinsic RA depolarization as sensed the RA lead to the LA cardiomechanical activation as detected using the implantable detector;
determining an EMOAT-1r value representing a time delay from an RA-paced LA depolarization to the LA cardiomechanical activation as detected using the implantable detector; and
determining an EMOAT-2r value representing a time delay from an RA pace to the LA cardiomechanical activation as detected using the implantable detector.

14. The method of claim 13 for use with a device wherein an RA electrode is used to detect atrial events via the RA and wherein setting the AVD values based on the EMOAT values includes setting the AVD equal to EMOAT-2+ where:
EMOAT-2+ is set equal to EMOAT2i plus a first offset for use with intrinsic atrial events sensed in the RA via an RA electrode; and
EMOAT-2+ is instead equal to EMOAT2r plus a second offset for use with paced atrial events.

15. The method of claim 14 wherein controlling pacing using the pacing delays includes:
sensing atrial events using an RA sensing vector;
for LV first pacing, pacing the LV using AVD applied to atrial events sensed or paced using the RA vector and then pacing the RV using AVD plus VVD; and
for RV first pacing, pacing the RV using AVD minus VVD applied to atrial events sensed using the RA vector and then pacing the LV using AVD.

16. The method of claim 13 for use with a device wherein the P4 electrode is used to detect atrial events via the LA and wherein setting the AVD values based on the EMOAT values includes setting the AVD equal to EMOAT-1+ where:
EMOAT-1+ is equal to EMOAT1i plus an offset for use with intrinsic atrial events sensed in the LA via a P4 electrode; and
EMOAT-1+ is equal to EMOAT1r plus an offset for use with paced atrial events.

17. The method of claim 16 wherein controlling pacing using the pacing delays includes:
sensing atrial events using a P4 sensing vector;
for LV first pacing, pacing the LV using AVD applied to atrial events sensed using the P4 vector and then pacing the RV using AVD plus VVD; and
for RV first pacing, pacing the RV using AVD minus VVD applied to atrial events sensed using the P4 vector and then pacing the LV using AVD.

18. A system for use with an implantable cardiac stimulation device equipped with a left ventricular (LV) lead having at least one proximal electrode implanted near an atrioventricular (AV) groove of the heart of the patient, the system comprising:
a left atrial (LA) cardioelectrical event sensor operative to sense an LA cardioelectrical event using the proximal electrode of the LV lead;
an LA cardiomechanical event detector operative to detect an LA cardiomechanical event responsive to the sensed electrical event utilizing at least one of echocardiography, sonocardiography and impedance cardiography, wherein the LA cardiomechanical event corresponds to one or more of: i) completion of an atrial kick, ii) closure of a mitral valve, and iii) onset, peak and/or completion of an A-wave of a mitral valve annulus;

an LA electromechanical delay determination system operative to determine an LA electromechanical delay between the LA cardioelectrical event and the LA cardiomechanical event;

an LA electromechanical delay-based pacing determination system operative to determine pacing delays based on the LA electro-mechanical delay for use in delivering pacing using the lead; and a pacing controller operative to controlling pacing using the pacing delays.

19. A system for use with an implantable cardiac stimulation device equipped with a left ventricular (LV) lead having at least one proximal electrode implanted near an atrioventricular (AV) groove of the heart of the patient, the system comprising:

means for sensing a left atrial (LA) cardioelectrical event using the proximal electrode of the LV lead;

means for detecting a LA cardiomechanical event responsive to the sensed electrical event utilizing at least one of echocardiography, sonocardiography and impedance cardiography, wherein the LA cardiomechanical event corresponds to one or more of: i) completion of an atrial kick, ii) closure of a mitral valve, and iii) onset, peak and/or completion of an A-wave of a mitral valve annulus;

means for determining an LA electromechanical delay between the LA cardioelectrical event and the LA cardiomechanical event;

means for determining pacing delays based on the LA electromechanical delay for use in delivering pacing using the lead; and means for controlling pacing using the pacing delays.

20. The system of claim 18 further comprising:

an RA cardioelectric event sensor operative to sense an RA cardioelectric event using an electrode of an RA lead;

the LA cardiomechanical event detector detecting an LA cardiomechanical event in response to the RA cardioelectric event sensed;

an RA-LA electromechanical delay determination system operative to determine an RA-LA electromechanical delay between the RA cardioelectric event and the LA cardiomechanical event;

an RA-LA delay determination system operative to determine pacing delays based on the RA-LA electromechanical delay for use in delivering pacing using the RA lead.

21. The system of claim 18 wherein the LA cardioelectric event corresponds to electrical depolarization of the LA.

22. The system of claim 18 wherein the LA electromechanical delay based pacing determination system is operative to determine the pacing delays to include an AV pacing delay for use with bi-ventricular cardiac resynchronization therapy (CRT).

23. The system of claim 18 wherein the LA electromechanical delay determination system is operative to determine the pacing delays in order to set a pacing delay to provide for delivery of an LV pacing pulse at a time of optimal left-heart filling.

24. The system of claim 18 further comprising an implantable device equipped for bi-ventricular pacing wherein the LV lead is a multi-polar lead having a proximal electrode (P4) implanted near the AV groove and wherein the implantable device defines a sensing vector coupled to the P4 electrode for sensing the LA cardioelectric event.

25. The system of claim 18 further comprising an implantable device coupled to a multi-polar LV lead having a proximal electrode (P4) implanted near the AV groove, the implantable device coupled to at least one of an RV lead having an RV coil electrode and an RA lead having a RA ring electrode, the implantable device including sensing circuitry to define a P4 sensing vector that includes one or more of: a P4-case vector, a P4-RV coil vector, a P4-RA ring vector, a P4-non P4 LV electrode vector and a P4-any other electrode in the heart vector.

26. The system of claim 18 wherein the LA cardiomechanical event detector represents at least one of an echocardiography detector, a sonocardiography detector and an impedance cardiography detector.

27. The system of claim 18 wherein the LA cardiomechanical event detector includes an ultrasound detector configured to detect one or more of the onset or completion of an A-wave of transmitrial flow, to detect a mitral valve closure time, and/or detect onset, peak or completion of an A-wave of the mitral valve annulus.

28. The system of claim 18 wherein the LA cardiomechanical event detector represents a sonocardiography detector configured to detect a first onset time of an S1 heart sound corresponding to a mitral valve closure time.

29. The system of claim 18 wherein the LA cardiomechanical event detector represents an impedance detector configured to detect a time of maximum cardiogenic impedance, or a time of maximum time derivative of cardiogenic impedance between RA and P4 electrodes, indicating completion or onset, respectively, of atrial kick into ventricles.

* * * * *